US006884748B2

(12) United States Patent
McCullough

(10) Patent No.: US 6,884,748 B2
(45) Date of Patent: Apr. 26, 2005

(54) PROCESS FOR PRODUCING FLUORINATED CATALYSTS

(75) Inventor: Laughlin G. McCullough, League City, TX (US)

(73) Assignee: Univation Technologies, LLC, Houston, TX (US)

( * ) Notice: Subject to any disclaimer, the term of this patent is extended or adjusted under 35 U.S.C. 154(b) by 177 days.

(21) Appl. No.: 10/368,581

(22) Filed: Feb. 18, 2003

(65) Prior Publication Data

US 2004/0043893 A1 Mar. 4, 2004

Related U.S. Application Data

(60) Provisional application No. 60/408,480, filed on Sep. 4, 2002.

(51) Int. Cl.[7] .......................... B01J 31/00; B01J 37/00; C08F 4/02; C08F 1/60
(52) U.S. Cl. ......................... 502/117; 526/165; 556/9; 556/27; 556/170; 556/400
(58) Field of Search ........................ 502/117; 526/165; 556/9, 27, 170, 400

(56) References Cited

U.S. PATENT DOCUMENTS

| 3,896,179 | A |   | 7/1975 | Resnick ...................... 260/616 |
| 4,874,880 | A |   | 10/1989 | Miya et al. .................... 556/53 |
| 5,525,678 | A |   | 6/1996 | Mink et al. .................. 525/246 |
| 5,602,067 | A |   | 2/1997 | Nowlin et al. .............. 502/104 |
| 5,614,456 | A |   | 3/1997 | Mink et al. .................. 502/115 |
| 5,637,772 | A | * | 6/1997 | Malik et al. ................. 564/505 |
| 5,723,705 | A |   | 3/1998 | Herrmann et al. ............. 585/9 |
| 5,750,813 | A |   | 5/1998 | Hess et al. .................... 585/12 |
| 6,096,845 | A |   | 8/2000 | Rosch et al. ................ 526/160 |
| 6,291,615 | B1 |   | 9/2001 | Dauben et al. ............. 526/160 |
| 6,303,718 | B1 |   | 10/2001 | Becke et al. ................ 526/160 |
| 6,410,474 | B1 |   | 6/2002 | Nowlin et al. .............. 502/113 |
| 6,417,130 | B1 |   | 7/2002 | Mink et al. .................. 502/113 |
| 6,423,664 | B1 | * | 7/2002 | Marchal-George et al. . 502/229 |
| 6,423,792 | B1 | * | 7/2002 | Debras et al. ............... 526/106 |
| 6,541,580 | B1 | * | 4/2003 | Matyjaszewski et al. ..... 526/90 |
| 6,627,764 | B1 | * | 9/2003 | Schottek et al. ............... 556/11 |
| 6,632,901 | B1 | * | 10/2003 | McCullough ................ 526/165 |
| 6,667,272 | B1 | * | 12/2003 | Speca .......................... 502/402 |
| 6,667,274 | B1 | * | 12/2003 | Hawley et al. ............. 502/415 |
| 6,686,306 | B1 | * | 2/2004 | Shih ........................... 502/113 |
| 6,753,390 | B1 | * | 6/2004 | Ehrman et al. ............. 526/113 |
| 2002/0032287 | A1 |   | 3/2002 | McCullough ................ 526/68 |
| 2002/0143125 | A1 | * | 10/2002 | Kaminsky et al. | |

FOREIGN PATENT DOCUMENTS

| DE | 4332009 A1 | 3/1995 | | |
| EP | 0200351 A2 | 11/1986 | | |
| EP | 0511665 A2 | 11/1992 | | |
| EP | 0519746 A1 | 12/1992 | | |
| EP | 0593083 A1 | 4/1994 | | |
| EP | 0705849 A1 | 12/1994 | | |
| EP | 0664301 A1 | 7/1995 | | |
| EP | 0965601 A1 | 12/1999 | | |
| EP | 1255792 A1 | 8/2001 | | |
| WO | WO 97/07141 | 2/1997 | | |
| WO | WO 97/46599 | 12/1997 | | |
| WO | WO 98/02247 | 1/1998 | | |
| WO | WO 98/28350 | 7/1998 | | |
| WO | WO 98/34724 | 8/1998 | | |
| WO | WO 99/03899 | 1/1999 | | |
| WO | wo 00/11047 A1 | * 3/2000 | ........... C08F/10/00 |
| WO | WO 00/11047 | 3/2000 | | |
| WO | WO 00/31088 | 6/2000 | | |
| WO | WO 01/23442 A1 | 4/2001 | | |
| WO | WO 01/60926 A1 | 8/2001 | | |

OTHER PUBLICATIONS

U.S. Appl. No. 10/290,122.*
J. Am. Chem. Soc. 1996, 118, 6784–6785. Verdaguer, et al., "Highly Enantioselective Imine Hydrosilation Using (S, S)–Ethylenebis(eta5–tetrahydroindenyl)titanium Difluoride".*
Organometallics 1998, 17, 3937–3944, Xie, et al. "Synthesis, Molecular Structure, and Reactivity of Organolanthanide . . . ".*
Organometallics 1999, 18, 3170–3177. Edelbach, et al., "Carbon–Fluorine Bond Cleavage by Zirconium Metal Hydride Complexes".*
Chem. Rev. 1997, 97, 3425–3468. Murphy, et al. "Organometallic Fluorides: Compounds Containing Carbon–Metal–Fluorine Fragments of d–Block Metals".*

(Continued)

*Primary Examiner*—Mark L. Bell
*Assistant Examiner*—Jennine M. Brown
(74) *Attorney, Agent, or Firm*—Kevin M. Faulkner

(57) ABSTRACT

The present invention relates to a process of producing a fluorided catalyst compound, catalyst compositions, and polymerization methods including such. At least one specific embodiment of the invention includes contacting a chlorinated metallocene catalyst component with a fluorinated inorganic salt, for a time sufficient to form a fluorinated metallocene catalyst component such as described in the following example:

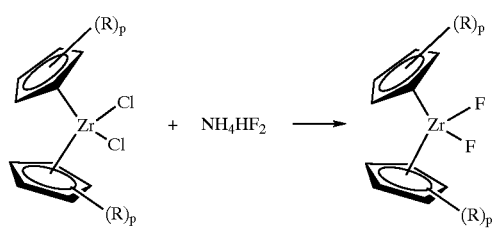

wherein R are substituent groups selected from the group consisting of $C_1$ to $C_{10}$ alkyls in a particular embodiment, and p is 0 or an integer from 1 to 5. The fluorinated inorganic salt is characterized in a particular embodiment as a compound that provides at least one fluoride ion when contacted with a diluent comprising at least 50 wt % water.

31 Claims, No Drawings

OTHER PUBLICATIONS

P.M. Druce et al., *Metallocene Halides. Part I. Synthesis, Spectra, and Redistribution Equilibria of Di–π–Cyclopentadienyldihalogeno–titanium(iv),–zirconium–(iv), and –hafnium(iv)*, J. Chem. Soc.(A), 2106–2110, (1969).

F. Garbassi et al., *XPS study of metallocene based catalysts for the polymerization of ethylene*, Journal of Molecular Catalysis A: Chemical 101, 199–209, (1995).

Axel Herzog et al., *Reactions of ($\eta^5$–$C_5$ $Me_5$)$ZrF_3$, ($\eta^5$ $C_5Me_4$ $Et$)$ZrF_3$, ($\eta^5$–$C_5Me_5$)$_2ZrF_2$, ($\eta^5$–$C_5Me_5$) $HfF_3$, and ($\eta^5$–$C_5Me_5$)$TaF_4$ with $AlMe_3$. Structure of the First Hafnium–Aluminum–Carbon Cluster*, Organometallics 15, 909–917, (1996).

Eamonn F. Murphy et al., *Synthesis and spectroscopic characterization of a series of substitued cyclopentadienyl Group 4 fluorides; crystal structure of the acetylacetonato complex [(acac)$_2$($\eta C_5Me_5$)$Zr$($\mu$–$F$)$SnMe_3Cl$]*, J. Chem. Soc., Dalton Trwans. 1983–1987 (1996).

Z. Xie et al., *Synthesis, Molecular Structure, and Reactivity of Organolanthanide Fluoride Complexes, [{(Me$_3$Si)$_2$C$_5$H$_3$}$_2$Ln($\mu$–F)]$_2$ (Ln=La, Nd, Sm, Gd) and [(C$_5$H$_{50}$)$_2$Ln($\mu$–F)(THF)]$_2$ (Ln=Y, Yb)*, 17 Organometallics 3937–3944 (1998).

U.S. Appl. No. filed concurrently, Fred D. Ehrman, et al., *Gas–Phase Polymerization Process*.

U.S. Appl. No. filed concurrently, Chi–I Kuo et al., *Bimodal Polyolefin Production Process and Films Therefrom*.

E.F. Murphy et al. in *Organometallic Fluorides: Compounds Containing Carbon–Metal–Fluorine Fragments of d–Block Metals*, 97 Chem. Rev. 3425–3468 (1997).

W.W. Lukens, Jr. et al. in *A π–Donor Spectrochemical Series for X in (Me$_5$C$_5$)$_2$TiX, and β–Agostic Interactions in X=Et and N(Me)Ph*, 118 J. Am. Chem. Soc. 1729–1728 (1996).

W. Kaminsky, et al., *Fluorinated Half–Sandwich Complexes as Catalysts in Syndiospecific Styrene Polymerization*, 30(25) Macromolecules 7647–7650 (1997).

* cited by examiner

PROCESS FOR PRODUCING FLUORINATED CATALYSTS

CROSS-REFERENCE TO RELATED APPLICATION

The present application claims priority to U.S. Provisional Patent Application U.S. Ser. No. 60/408,480 filed Sep. 4, 2002.

FIELD OF INVENTION

This application relates to a process for forming fluorinated catalyst compounds, and in particular, to producing fluorided metallocene catalyst components and using them as part of a bimodal catalyst composition.

BACKGROUND

Bimodal polymers produced using two or more different catalyst types—bimetallic catalysts—are of increasing interest, especially in producing polyethylene and other polyolefins. See, for example, U.S. Pat. No. 5,525,678. However, problems exist in using these bimetallic catalysts, especially in the gas phase. One problem is catalyst activity, which should be as high as possible in order to economize the process, as catalysts costs are significant.

One method of improving catalyst efficiency in gas phase processes is to improve upon the catalyst used in the process. A promising class of single-site catalysts for commercial use includes those wherein the metal center has at least one extractable fluorine (or fluorine "leaving group"). Disclosures of such catalysts include U.S. Pat. No. 20020032287; U.S. Pat. No. 6,303,718; U.S. Pat. No. 6,291,615; U.S. Pat. No. 4,874,880; U.S. Pat. No. 3,896,179; WO 97/07141; DE 43 32 009 A1; EP-A2 0 200 351; EP-A1 0 705 849; E. F. Murphy, et al., *Synthesis and spectroscopic characterization of a series of substituted cyclopentadienyl Group 4 fluorides; crystal structure of the acetylacetonato complex* [(acac)$_2$($\eta^5$-C$_5$Me$_5$)Zr($\mu$-F)SnMe$_3$Cl], DALTON, 1983 (1996); A. Herzog, et al., *Reactions of* ($\eta^5$-C$_5$Me$_5$)ZrF$_3$, ($\eta^5$-C$_5$Me$_4$Et)ZrF$_3$, ($\eta^5$-C$_5$M4$_5$)$_2$ZrF$_2$, ($\eta^5$-C$_5$Me$_5$)HfF$_3$, *and* ($\eta^5$-C$_5$Me$_5$)TaF$_4$ *with AlMe$_3$, Structure of the First Hafnium-Aluminum-Carbon Cluster*, 15 ORGANOMETALLICS 909–917 (1996); F. Garbassi, et al., JOURNAL OF MOLECULAR CATALYSIS A: CHEMICAL 101 199–209 (1995); and W. Kaminsky, et al., *Fluorinated Half-Sandwich Complexes as Catalysts in Syndiospecific Styrene Polymerization*, 30(25) MACROMOLECULES 7647–7650 (1997). Use of such single site catalyst components in a olefin polymerization system is desirable, especially in gas-phase polyethylene polymerization. However, it is often not commercially practical to produce such fluorided metallocene catalysts.

Methods of fluoriding metallocene catalyst components are disclosed by Z. Xie et al., *Synthesis, Molecular Structure, and Reactivity of Organolanthanide Fluoride Complexes*, [{(Me$_3$Si)$_2$C$_5$H$_3$}$_2$Ln($\mu$-F)]$_2$ (Ln=La, Nd, Sm, Gd) *and* [(C$_5$H$_5$)$_2$Ln($\mu$-F)(THF)]$_2$ (Ln=Y, Yb), 17 ORGANOMETALLICS 3937–3944 (1998); E. F. Murphy et al. in *Organometallic Fluorides: Compounds Containing Carbon—Metal—Fluorine Fragments of d-Block Metals*, 97 CHEM. REV. 3425–3468 (1997); W. W. Lukens, Jr. et al. in *A π-Donor Spectrochemical Series for X in* (Me$_5$C$_5$)$_2$TiX, *and β-Agostic Interactions in X=Et and N(Me)Ph*, 118 J. AM. CHEM. SOC. 1729–1728 (1996); and P. M. Druce et al. in *Metallocene Halides: Part I. Synthesis, Spectra, and Redistribution Equilibria of Di-π-cyclopentadienyl-Ti(IV), —Zr (IV), and —Hf(IV)*, 14 J. CHEM. SOC. 2106–2110 (1969). However, these methods fall short of a desirable, cost effect commercial method of making fluorided metallocene catalyst components. It would be desirable to improve the method of producing fluorided metallocenes, as well as its us in bimodal polymerization processes, especially for bimodal gas phase polymerization processes. The present invention is directed towards solving this and other problems.

SUMMARY

This invention relates to a process for producing fluorided metallocene compounds, a catalyst composition comprising such compounds, and a method of polymerizing olefins using such compounds.

At least one specific embodiment of the invention includes contacting a metallocene catalyst component, a chlorinated metallocene catalyst compound in a particular embodiment, with a fluoriding agent for a time sufficient to form a fluorinated metallocene catalyst compound. In one or more specific embodiments, the fluoriding agent is or includes a fluorinated inorganic salt. In one or more specific embodiments, the fluoriding agent is in the form of, or part of, a mixture, for example, an aqueous solution.

Another specific embodiment of the invention is directed to a process of producing a fluorinated catalyst compound, which includes: contacting a metallocene compound having the general formula (CpR$_p$)$_m$MX$_{1-3}$ with a mixture comprising a fluorinated inorganic salt to form a fluorinated metallocene having the formula (CpR$_p$)$_m$MX$_n$F$_r$ (which can include, for example, a partially fluorinated metallocene) wherein Cp is a cyclopentadienyl ring or derivative thereof, R is a hydrocarbyl group, methyl group or hydrocarboxyl group, M is a Group 4, 5, or 6 transition metal, X is an anionic ligand such as a halogen, carboxylate, acetylacetonate, alkoxide, hydroxide, or oxide, m=1 to 3, p=0 to 10, n=0 to 3, and r=1 to 3.

Preferably, in any one of the processes identified above or described herein, the fluoriding agent is a mixture, for example, a mixture that comprises water and fluorinated inorganic salt. Alternatively, the mixture may comprise an organic solvent and the fluorinated inorganic salt. In certain embodiments, the fluoriding agent may be considered the inorganic fluoride salt itself. Various specific embodiments demonstrate unusually high yields in the presence of water. Surprisingly, for example, contacting the chlorinated metallocene described herein with the mixture results in a product yield of 50% or more. More particularly, contacting the chlorinated metallocene with the salt mixture results in a product yield of 80% or more. Even more particularly, contacting the chlorinated metallocene with the salt mixture results in a product yield of 90% or more.

In a specific embodiment, M is selected from the group consisting of titanium, zirconium, hafnium, vanadium, niobium, tantalum, chromium, molybdenum, tungsten and combinations thereof. In a more particular embodiment, M is zirconium or hafnium. In another embodiment, the fluorinated metallocene is bridged. In yet another embodiment, p is 0. In a particular embodiment, p is 1 or more (Cp is substituted). In a particular embodiment, p is 2 or more (Cp is disubstituted).

DETAILED DESCRIPTION

General Definitions

As used herein, in reference to Periodic Table "Groups" of Elements, the "new" numbering scheme for the Periodic Table Groups are used as in the CRC HANDBOOK OF CHEMISTRY AND PHYSICS (David R. Lide ed., CRC Press 81$^{st}$ ed. 2000).

As used herein, the phrase "catalyst system" includes at least one "catalyst component" and at least one "activator", both of which are described further herein. The catalyst system may also include other components, such as supports, etc., and is not limited to the catalyst component and/or activator alone or in combination. The catalyst system may include any number of catalyst components in any combination as described herein, as well as any activator in any combination as described herein.

As used herein, the phrase "catalyst compound" includes any compound that, once appropriately activated, is capable of catalyzing the polymerization or oligomerization of olefins, the catalyst compound comprising at least one Group 3 to Group 12 atom, and optionally at least one leaving group bound thereto.

As used herein, the phrase "leaving group" refers to one or more chemical moieties bound to the metal center of the catalyst component that can be abstracted from the catalyst component by an activator, thus producing the species active towards olefin polymerization or oligomerization. The activator is described further below.

As used herein, the term "fluorided metallocene catalyst component" or "fluorided catalyst component" means a catalyst compound having at least one fluoride or fluorine containing leaving group, preferably a metallocene or metallocene-type catalyst compound having at least one fluoride or fluorine containing leaving group.

As used herein, a "hydrocarbyl" includes aliphatic, cyclic, olefinic, acetylenic and aromatic radicals (i.e., hydrocarbon radicals) comprising hydrogen and carbon that are deficient by one hydrogen. A "hydrocarbylene" is deficient by two hydrogens.

As used herein, an "alkyl" includes linear, branched and cyclic paraffin radicals that are deficient by one hydrogen. Thus, for example, a —$CH_3$ group ("methyl") and a $CH_3CH_2$— group ("ethyl") are examples of alkyls.

As used herein, an "alkenyl" includes linear, branched and cyclic olefin radicals that are deficient by one hydrogen; alkynyl radicals include linear, branched and cyclic acetylene radicals deficient by one hydrogen radical.

As used herein, "aryl" groups includes phenyl, naphthyl, pyridyl and other radicals whose molecules have the ring structure characteristic of benzene, naphthylene, phenanthrene, anthracene, etc. For example, a $C_6H_5^-$ aromatic structure is an "phenyl", a $C_6H_4^{2-}$ aromatic structure is an "phenylene". An "arylalkyl" group is an alkyl group having an aryl group pendant therefrom; an "alkylaryl" is an aryl group having one or more alkyl groups pendant therefrom.

As used herein, an "alkylene" includes linear, branched and cyclic hydrocarbon radicals deficient by two hydrogens. Thus, —$CH_2$— ("methylene") and —$CH_2CH_2$— ("ethylene") are examples of alkylene groups. Other groups deficient by two hydrogen radicals include "arylene" and "alkenylene".

As used herein, the phrase "heteroatom" includes any atom other than carbon and hydrogen that can be bound to carbon, and in one embodiment is selected from the group consisting of B, Al, Si, Ge, N, P, O, and S. A "heteroatom-containing group" is a hydrocarbon radical that contains a heteroatom and may contain one or more of the same or different heteroatoms, and from 1 to 3 heteroatoms in a particular embodiment. Non-limiting examples of heteroatom-containing groups include radicals of imines, amines, oxides, phosphines, ethers, ketones, oxoazolines heterocyclics, oxazolines, thioethers, and the like.

As used herein, an "alkylcarboxylate", "arylcarboxylate", and "alkylarylcarboxylate" is an alkyl, aryl, and alkylaryl, respectively, that possesses a carboxyl group in any position. Examples include $C_6H_5CH_2C(O)O^-$, $CH_3C(O)O^-$, etc.

As used herein, the term "substituted" means that the group following that term possesses at least one moiety in place of one or more hydrogens in any position, the moieties selected from such groups as halogen radicals (esp., Cl, F, Br), hydroxyl groups, carbonyl groups, carboxyl groups, amine groups, phosphine groups, alkoxy groups, phenyl groups, naphthyl groups, $C_1$ to $C_{10}$ alkyl groups, $C_2$ to $C_{10}$ alkenyl groups, and combinations thereof. Examples of substituted alkyls and aryls includes, but are not limited to, acyl radicals, alkylamino radicals, alkoxy radicals, aryloxy radicals, alkylthio radicals, dialkylamino radicals, alkoxycarbonyl radicals, aryloxycarbonyl radicals, carbomoyl radicals, alkyl- and dialkyl-carbamoyl radicals, acyloxy radicals, acylamino radicals, arylamino radicals, and combinations thereof.

As used herein, structural formulas are employed as is commonly understood in the chemical arts; lines ("—") used to represent associations between a metal atom ("M", Group 3 to Group 12 atoms) and a ligand or ligand atom (e.g., cyclopentadienyl, nitrogen, oxygen, halogen ions, alkyl, etc.), as well as the phrases "associated with", "bonded to" and "bonding", are not limited to representing a particular type of chemical bond, as these lines and phrases are meant to represent a "chemical bond"; a "chemical bond" defined as an attractive force between atoms that is strong enough to permit the combined aggregate to function as a unit, or "compound".

A certain stereochemistry for a given structure or part of a structure should not be implied unless so stated for a given structure or apparent by use of commonly used bonding symbols such as by dashed lines and/or heavy lines.

Unless stated otherwise, no embodiment of the present invention is herein limited to the oxidation state of the metal atom "M" as defined below in the individual descriptions and examples that follow. The ligation of the metal atom "M" is such that the compounds described herein are neutral, unless otherwise indicated.

As used herein, the term "bimodal," when used to describe a polymer or polymer composition (e.g., polyolefins such as polypropylene or polyethylene, or other homopolymers, copolymers or terpolymers) means "bimodal molecular weight distribution," which is understood as having the broadest definition persons in the pertinent art have given that term as reflected in printed publications and issued patents. For example, a single composition that includes polyolefins with at least one identifiable high molecular weight distribution and polyolefins with at least one identifiable low molecular weight distribution is considered to be a "bimodal" polyolefin, as that term is used herein. In a particular embodiment, other than having different molecular weights, the high molecular weight polyolefin and the low molecular weight polyolefin are essentially the same type of polymer, for example, polypropylene or polyethylene.

As used herein, the term "productivity" means the weight of polymer produced per weight of the catalyst used in the polymerization process (e.g., grams polymer/gram catalyst).

As used herein, the term "dehydrated" is understood as having the broadest definition persons in the pertinent art have given that term in describing catalyst support materials, for example, silica, as reflected in printed publications and issued patents, and includes any material, for example, a support particle, from which a majority of the contained/adsorbed water has been removed.

As used herein, the term "salt" means a chemical compound that may be formed by a chemical reaction of an acid and a base.

As used herein, the term "fluoriding agent" is defined as any inorganic compound or combination of two or more inorganic compounds capable of forming at least one bonding association between a fluorine or fluorine-containing moiety and a target compound. The fluoriding agent can be any inorganic compound or combination of two or more inorganic compounds that includes one or more fluorine atoms, and more particularly, a fluorinated inorganic salt. The "target compound" can be any compound capable of forming a bonding association with a fluorine ion, examples of which include Group 3 to 12 metals and metal compounds, and desirably, Group 3 to 6 metallocene compounds. Non-limiting examples of "fluorine-containing moieties" include fluorine ions and radicals.

As used herein, the term "product yield" means the weight of product produced per weight of maximum product possible (e.g., grams fluorinated catalyst per gram of theoretical fluorinated catalyst).

Process for Making a Fluorinated Catalyst Compound

Embodiments of the invention include a process of producing a fluorinated catalyst compound, and in particular, a fluorided metallocene catalyst component. The fluorided metallocene itself is described in more detail below. The fluorided metallocene catalyst component can be, for example, any one of the catalysts described in greater detail below, or the "second catalyst component" of the bimodal catalyst. The fluorided catalyst compound is preferably a metallocene type compound having the general formula $(Cp(R)_p)_m MX_n F_r$ (which can include, for example, a partially fluorinated metallocene), wherein Cp is a cyclopentadienyl ligand or ligand isolobal to cyclopentadienyl (as described further below) that can be substituted in any position by a group R as set out below, M is a Group 4, 5, or 6 transition metal in a particular embodiment, X is an anionic ligand such as a halogen, carboxylate, acetylacetonate, alkoxide, hydroxide, or oxide; p is an integer from 0 to 10, m is an integer from 1 to 3, n is an integer from 0 to 3, and r is an integer from 1 to 3; in a particular embodiment, m is 2, n is 0 and r is 2. If m is 2, the Cps may be bridged by a group (A) as described further below.

The process includes contacting a metallocene catalyst compound with a fluoriding agent, and more particularly, a fluorinated inorganic salt, for a time sufficient to form the fluorided metallocene catalyst compound. The metallocene catalyst compound preferably has the same general formula as the desired fluorinated metallocene compound, with the exception that the one or more leaving groups X are an anionic ligand (e.g., chlorine or bromine) rather than fluorine. The metallocene compound that is contacted with the fluoriding agent may be commercially available, or may be prepared by methods known to one skilled in the art.

The metallocene compound may include a cyclopentadienyl ligand or ligand isolobal to Cp, either substituted or unsubstituted. The amount of substitution on the Cp may affect the yield of the fluorinated metallocene compound. Therefore, at least one Cp of the metallocene is substituted in one embodiment, and two Cps are substituted in another embodiment, wherein the metallocene is a sandwich metallocene as set out below. In a particular embodiment, the substituent group (R) is not an aryl group such as phenyl, indenyl or fluorenyl. In at least certain embodiments, it has been discovered that benzene substituent groups correspond to reduced product yields. For example, when R is indenyl, the product yield may be as low as zero. Preferably, the substituent groups include hydrocarbyl groups. In a preferred embodiment, alkyl substitution results in surprisingly high yields, for example, 95% or more.

In one embodiment, the fluoriding agent is a fluorinated inorganic salt or combination of salts described by the general formula (a):

$$[\alpha]_a [\beta]_b, \qquad (a)$$

wherein α is a cationic species selected from the group consisting of Group 1 and 2 cations, anilinium and substituted versions thereof, and $NH_4^+$, $NH_3R$, $NH_2R_2$, and $NHR_3^+$ wherein R is selected from the group consisting of hydride, chloride, $C_1$ to $C_{10}$ alkyl and $C_6$ to $C_{12}$ aryls;

β is an anionic species selected from the group consisting of fluorine ions and compounds comprising fluorine and one or more elements selected from the group consisting of hydrogen, silicon, carbon, phosphorous, oxygen, aluminum and boron; and a and b are integers from 1 to 10.

In a particular embodiment, the fluorinated inorganic salt is a compound characterized in that it is capable of generating fluoride ions when contacted with water or other protic diluent. Non-limiting examples of the fluorinated inorganic salt include $(NH_4)_3 AlF_6$, $NH_4 HF_2$, $NaF$, $KF$, $NH_4 F$, $(NH_4)_2 SiF_6$ and combinations thereof.

The fluorinated inorganic malt compound may include a fluorinated inorganic salt mixture. The fluorinated inorganic salt compound is preferably soluble or partially soluble in a diluent. Therefore, the mixture may include the fluorinated inorganic salt and a diluent, that is, the fluorinated inorganic salt may be dissolved in a diluent prior to contacting the metallocene catalyst compound. The diluent may include an organic diluent. In a particular embodiment, the diluent is water or water in combination with some other polar diluent that is miscible with water (e.g., ethers, ketones, aldehydes, etc). In another embodiment, the diluent is any desirable protic medium. In a particular embodiment, the fluorinated inorganic salt is combined with a diluent comprising at least 10 wt % water, and that is at least 50 wt % water in another embodiment and at least 60 wt % water in another embodiment, and at least 70 wt % water in yet another embodiment, and at least 80 wt % water in yet another embodiment, and at least 90 wt % in a particular embodiment, and at least 99 wt % water in a more particular embodiment.

The metallocene compound that is contacted with the fluoriding agent may be initially charged in an inert or non-protic diluent. The inert diluent may include one of, or a mixture of, aliphatic and aromatic hydrocarbons or a halogenated solvent. Suitable hydrocarbons include substituted and unsubstituted aliphatic hydrocarbons and substituted and unsubstituted aromatic hydrocarbons. In a particular embodiment, the inert diluent is selected from the group consisting of $C_3$ to $C_{30}$ hydrocarbons and $C_1$ to $C_{10}$ halogenated hydrocarbons and mixtures thereof in a particular embodiment. Non-limiting examples of suitable inert diluents include hexane, heptane, octane, decane, toluene, xylene, dichloromethane, dichloroethane, chloroform and 1-chlorobutane.

In a particular embodiment of the method of fluoriding metallocenes described herein, the fluorinated inorganic salt combined with a protic diluent is reacted with the metallocene combined with an inert diluent. In a more particular embodiment, the fluorinated inorganic salt in at least 50% water is combined with the metallocene to be fluorided dissolved/suspended in a hydrocarbon or halogenated hydrocarbon diluent. The combined reactants may form two or more phases in contact with one another. The fluoriding reaction then takes place under desirable mixing and temperature conditions.

In embodiments of the fluoriding step wherein the fluoriding agent is immiscible or only partially miscible with the diluent, it is within the scope of the invention to use a reagent that will assist the transport of the fluoriding agent to the alkylated catalyst component or the diluent phase in which the alkylated catalyst component exists, or assist in the reaction between the fluoriding agent and alkylated catalyst component. Such reagents—phase-transfer catalysts—are known in the art and are used in reactions wherein, for example, an aqueous or polar diluent phase is in contact with a non-polar or hydrocarbon diluent phase, and the reactants are separated as such. Non-limiting examples of such phase-transfer catalysts include quaternary ammonium salts (e.g., quaternary ammonium bisulfate), crown ethers, and others common in the art.

Depending on the desired degree of substitution, the ratio of fluorine (of the fluoriding agent) to metallocene combined to react is from 1 equivalent to 20 equivalents in one embodiment, and from 2 to 10 equivalents in another embodiment, and from 2 to 8 equivalents in yet another embodiment, and from 2 to 5 equivalents in yet another embodiment, wherein a desirable range comprises any combination of any upper limit with any lower limit. While excess fluorinated inorganic salt may not be detrimental, the molar ratio of the reactants is preferably determined by the number of anionic ligands to be substituted in the metallocene compound, that is, the number of anionic ligands to be replace by fluorine or fluoride atoms. In a particular embodiment, the number of anionic ligands to be substituted is 2.

Stated another way, the desired amount of fluoriding agent, based on the equivalents of fluorine in the fluoriding agent, that is combined with the metallocene catalyst compound ranges from 1, or 2, or 3, or 4, or 5 to 6, or 7, or 8, or 10, or 12, or 14 or 15 or 18 or 20, wherein a desirable range comprises any combination of any upper limit with any lower limit described herein. In another embodiment, the desired amount of fluoriding agent, based on the equivalents of fluoriding agent as a whole, ranges from 1, or 2, or 3, or 4 to 5 or 6, or 7, or 8, or 9, or 10, wherein a desirable range comprises any combination of any upper limit with any lower limit described herein.

The fluorinated inorganic salt may be reacted with the metallocene compound by vigorously stirring the compounds. The reaction may occur at any temperature that affords the desired mono, di or trifluorided metallocene, including temperatures of from −80° C. to 120° C. in one embodiment, and from 0 to 100° C. in a more particular embodiment, and from 10 to 60° C. in yet more particular embodiment, and from 15 to 40° C. in yet a more particular embodiment. At those temperatures, reaction times of 0.05 hour to 8 hours are sufficient to form a fluorinated metallocene compound, but routine experimentation may be desirable to arrive at an optimum temperature. Generally, the reaction time is dependent upon the amount of reactants reacted. In one embodiment, the reaction time is from 0.1 hour to 3 hours.

The diluent, along with reaction by-products, can be removed from the mixture in a conventional manner, such as by evaporation or filtering, to obtain the dry, fluorinated metallocene compound. For example, the fluorided metallocene may be dried in the presence of magnesium sulfate. The filtrate, which contains the fluorinated metallocene compound in high purity and yield, can without further processing be directly used in the polymerization of olefins if the solvent is a hydrocarbon.

Contacting the metallocene compound with the fluorinated inorganic salt, an aqueous fluorinated inorganic salt, results in a product yield of 50% or more in a particular embodiment. The product yield is 80% or more in yet a more particular embodiment. The product yield is 90% or more in yet a more particular embodiment. Unexpectedly, contacting the metallocene compound with the aqueous solution of fluorinated inorganic salt results in a fluorided metallocene compound having high productivities.

Bimetallic Catalyst

As used herein, the term "bimetallic catalyst" or "bimetallic catalyst system" refers to two or more catalyst components used in combination with at least one activator, and optionally a support material, that is useful in polymerizing olefins. The "supported bimetallic catalyst" or "supported bimetallic catalyst composition" refers the bimetallic catalyst system as used in combination with a support material, wherein one or more of the components that make up the bimetallic catalyst system may be bound to the support. In a particular embodiment, the bimetallic catalyst of the invention includes two catalyst components. In a more particular embodiment, the bimetallic catalyst component includes a "first catalyst component" and a "second catalyst component".

As used herein, the term "first catalyst component" refers to any catalyst component other than the second catalyst component. Preferably, the first catalyst component is a non-metallocene catalyst component, examples of which include titanium or vanadium based Ziegler-Natta catalysts compounds as described further herein.

As used herein, the term "non-metallocene compound" refers any catalyst that is neither a metallocene nor one of the metallocene-type catalyst compounds identified below.

As used herein, the term "second catalyst component" refers to any catalyst that is different from a first catalyst component, a metallocene catalyst component in a particular embodiment. In a particular embodiment, the second catalyst component includes a fluorided metallocene component which comprises at least one fluoride ion leaving group or fluorine containing group.

Certain embodiments of the present invention involve contacting monomers with a bimetallic catalyst component, also referred to herein as simply a bimetallic catalyst. In a particular embodiment, each different catalyst compound that comprises the bimetallic catalyst resides, or is supported on a single type of support such that, on average, each particle of support material includes both the first and second catalyst components. In another embodiment, the first catalyst component is supported separately from the second catalyst component such that on average any given particle of support material comprises only the first or the second catalyst component. In this later embodiment, each supported catalyst may be introduced into the polymerization reactor sequentially in any order, alternately in parts, or simultaneously.

In a particular embodiment, the first catalyst component includes a titanium non-metallocene catalyst component, from which a higher molecular weight resin (e.g., >ca 100,000 amu) can be produced. In a particular embodiment, the second catalyst component includes a metallocene component, from which a lower molecular weight resin (e.g., <ca 100,000 amu) can be produced. Accordingly, polymerization in the presence of the first and second catalyst components provides a bimodal polyolefin composition that includes a low molecular weight component and a high molecular weight component. The two catalyst components reside on a single support particle in a particular embodiment, and they can be affixed to the support in a variety of ways.

In one embodiment, an "enhanced silica" is prepared as described herein and constitutes the support; the first catalyst component is a non-metallocene compound that is first combined with the enhanced silica, to provide a supported non-metallocene composition; the supported non-metallocene composition is combined with the second catalyst component, for example, a fluorided metallocene (a metallocene having at least one fluorine ion leaving group), resulting in a fluorinated bimetallic catalyst composition having enhanced productivity when used in production of a bimodal polyolefin composition.

Various methods of affixing two different catalyst components (albeit a different combination of catalysts) to a support can be used. In general, one procedure for preparing a supported bimetallic catalyst can include providing a supported first catalyst component, contacting a slurry that includes the first catalyst component in a non-polar hydrocarbon with a solution that includes the second catalyst component, which may also include an activator, and drying the resulting product that includes the first and second catalyst components and recovering a bimetallic catalyst composition.

First Catalyst Component

As noted above, the bimetallic catalyst composition includes a first catalyst component, which is (or includes) a non-metallocene compound. However, it is contemplated that for certain applications the first catalyst component may alternatively be a metallocene compound, or even one of the metallocene-type catalyst compounds identified below that is different in structure from the second catalyst component as described herein. In a particular embodiment, the first catalyst component is a Ziegler-Natta catalyst compound. Ziegler-Natta catalyst components are well known in the art and described by, for example, in ZIEGLER CATALYSTS 363–386 (G. Fink, R. Mulhaupt and H. H. Brintzinger, eds., Springer-Verlag 1995). Examples of such catalysts include those comprising $TiCl_4$ and other such transition metal oxides and chlorides.

The first catalyst component is combined with a support material in one embodiment, either with or without the second catalyst component. The first catalyst component can be combined with, placed on or otherwise affixed to a support in a variety of ways. In one of those ways, a slurry of the support in a suitable non-polar hydrocarbon diluent is contacted with an organomagnesium compound, which then dissolves in the non-polar hydrocarbon diluent of the slurry to form a solution from which the organomagnesium compound is then deposited onto the carrier. The organomagnesium compound can be represented by the formula RMgR', where R' and R are the same or different $C_2$–$C_{12}$ alkyl groups, or $C_4$–$C_{10}$ alkyl groups, or $C_4$–$C_8$ alkyl groups. In at least one specific embodiment, the organomagnesium compound is dibutyl magnesium. In one embodiment, the amount of organomagnesium compound included in the silica slurry is only that which will be deposited, physically or chemically, onto the support, for example, being bound to the hydoxyl groups on the support, and no more than that amount, since any excess organomagnesium compound may cause undesirable side reactions. Routine experimentation can be used to determine the optimum amount of organomagnesium compound. For example, the organomagnesium compound can be added to the slurry while stirring the slurry, until the organomagnesium compound is detected in the support solvent. Alternatively, the organomagnesium compound can be added in excess of the amount that is deposited onto the support, in which case any undeposited excess amount can be removed by filtration and washing.

The amount of organomagnesium compound (moles) based on the amount of dehydrated silica (grams) generally range from 0.2 mmol/g to 2 mmol/g.

Optionally, the organomagnesium compound-treated slurry is contacted with an electron donor, such as tetraethylorthosiloxane (TEOS) or an organic alcohol R"OH, where R" is a $C_1$–$C_{12}$ alkyl group, or a $C_1$ to $C_8$ alkyl group, or a $C_2$ to $C_4$ alkyl group. In a particular embodiment, R"OH is n-butanol. The amount of alcohol used in an amount effective to provide an R"OH:Mg mol/mol ratio of from 0.2 to 1.5, or from 0.4 to 1.2, or from 0.6 to 1.1, or from 0.9 to 1.0.

The organomagnesium and alcohol-treated slurry is contacted with a non-metallocene transition metal compound. Suitable non-metallocene transition metal compounds are compounds of Group 4 and 5 metals that are soluble in the non-polar hydrocarbon used to form the silica slurry. Suitable non-metallocene transition metal compounds include, for example, titanium and vanadium halides, oxyhalides or alkoxyhalides, such as titanium tetrachloride ($TiCl_4$), vanadium tetrachloride ($VCl_4$) and vanadium oxytrichloride ($VOCl_3$), and titanium and vanadium alkoxides, wherein the alkoxide moiety has a branched or unbranched alkyl group of 1 to 20 carbon atoms, preferably 1 to 6 carbon atoms. Mixtures of such transition metal compounds may also be used. The amount of non-metallocene transition metal compound used is sufficient to give a transition metal to magnesium mol/mol ratio of from 0.3 to 1.5, or from 0.5 to 0.8. The diluent can then be removed in a conventional manner, such as by evaporation or filtering, to obtain the dry, supported first catalyst component.

The first and second catalyst components may be contacted with the support in any order. In a particular embodiment of the invention, the first catalyst component is reacted first with the support as described above, followed by contacting this supported first catalyst component with a second catalyst component.

Fluorided Metallocene Catalyst Component

The fluorided metallocene is described more particularly herein. Further, the bimetallic catalyst system useful in the present invention includes at least one fluorided metallocene catalyst component as described herein. Metallocene catalyst compounds are generally described throughout in, for example, 1 & 2 METALLOCENE-BASED POLYOLEFINS (John Scheirs & W. Kaminsky eds., John Wiley & Sons, Ltd. 2000); G. G. Hlatky in 181 COORDINATION CHEM. REV. 243–296 (1999) and in particular, for use in the synthesis of polyethylene in 1 METALLOCENE-BASED POLYOLEFINS 261–377 (2000). The metallocene catalyst compounds as described herein include "half sandwich" and "full sandwich" compounds having one or more Cp ligands (cyclopentadienyl and ligands isolobal to cyclopentadienyl) bound to at least one Group 3 to Group 12 metal atom, and one or more leaving group(s) bound to the at least one metal atom. Hereinafter, these compounds will be referred to as "metallocenes" or "metallocene catalyst components". The fluorided metallocene components are those wherein at least one leaving group bound to M is a fluoride ion or a fluorine-containing group. The metallocene catalyst component is supported on a support material in a particular embodiment as described further below, and may be supported with or without the first catalyst component, with the first catalyst component in a particular embodiment.

The Cp ligands are typically π-bonded and/or fused ring(s) or ring systems. The ring(s) or ring system(s) typically comprise atoms selected from the group consisting of Groups 13 to 16 atoms, and more particularly, the atoms that make up the Cp ligands are selected from the group consisting of carbon, nitrogen, oxygen, silicon, sulfur, phosphorous, germanium, boron and aluminum and combinations thereof, wherein carbon makes up at least 50% of the ring members. Even more particularly, the Cp ligand(s) are selected from the group consisting of substituted and unsubstituted cyclopentadienyl ligands and ligands isolobal to cyclopentadienyl, non-limiting examples of which include cyclopentadienyl, indenyl, fluorenyl and other structures. Further non-limiting examples of such ligands include cyclopentadienyl, cyclopentaphenanthreneyl, indenyl, benzindenyl, fluorenyl, octahydrofluorenyl, cyclooctatetraenyl, cyclopentacyclododecene, phenanthrindenyl, 3,4-benzofluorenyl, 9-phenylfluorenyl, 8-H-cyclopent[a]acenaphthylenyl, 7H-dibenzofluorenyl, indeno[1,2-9]anthrene, thiophenoindenyl, thiophenofluorenyl, hydrogenated versions thereof (e.g., 4,5, 6,7-tetrahydroindenyl, or "H$_4$Ind"), substituted versions thereof, and heterocyclic versions thereof. In a particular embodiment, the metallocenes useful in the present invention are selected from those including one or two, two in a more particular embodiment, of the same or different Cp rings selected from the group consisting of cyclopentadienyl, indenyl, fluorenyl, tetrahydroindenyl, and substituted versions thereof.

The metal atom "M" of the metallocene catalyst compound, as described throughout the specification and claims, may be selected from the group consisting of Groups 3 through 12 atoms and lanthanide Group atoms in one embodiment; and selected from the group consisting of Groups 3 through 10 atoms in a more particular embodiment, and selected from the group consisting of Sc, Ti, Zr, Hf, V, Nb, Ta, Mn, Re, Fe, Ru, Os, Co, Rh, Ir, and Ni in yet a more particular embodiment; and selected from the group consisting of Groups 4, 5 and 6 atoms in yet a more particular embodiment, and a Ti, Zr, Hf atoms in yet a more particular embodiment, and Zr in yet a more particular embodiment. The oxidation state of the metal atom "M" may range from 0 to +7 in one embodiment; and in a more particular embodiment, is +1, +2, +3, +4 or +5; and in yet a more particular embodiment is +2, +3 or +4. The groups bound the metal atom "M" are such that the compounds described below in the formulas and structures are electrically neutral, unless otherwise indicated. The Cp ligand(s) form at least one chemical bond with the metal atom M to form the "metallocene catalyst compound". The Cp ligands are distinct from the leaving groups bound to the catalyst compound in that they are not highly susceptible to substitution/abstraction reactions.

In one aspect of the invention, the one or more metallocene catalyst components of the invention are represented by the formula (I):

$$Cp^A Cp^B MX_n \qquad (I)$$

wherein M is as described above; each X is chemically bonded to M; each Cp group is chemically bonded to M; and n is an integer from 0 to 4, and either 1 or 2 in a particular embodiment.

The ligands represented by $Cp^A$ and $Cp^B$ in formula (I) may be the same or different cyclopentadienyl ligands or ligands isolobal to cyclopentadienyl, either or both of which may contain heteroatoms and either or both of which may be substituted by a group R. In one embodiment, $Cp^A$ and $Cp^B$ are independently selected from the group consisting of cyclopentadienyl, indenyl, tetrahydroindenyl, fluorenyl, and substituted derivatives of each.

Independently, each $Cp^A$ and $Cp^B$ of formula (I) may be unsubstituted or substituted with any one or combination of substituent groups R. Non-limiting examples of substituent groups R as used in structure (I) as well as ring substituents in structures (Va-d) include groups selected from the group consisting of hydrogen radicals, alkyls, alkenyls, alkynyls, cycloalkyls, aryls, acyls, aroyls, alkoxys, aryloxys, alkylthiols, dialkylamines, alkylamidos, alkoxycarbonyls, aryloxycarbonyls, carbomoyls, alkyl- and dialkyl-carbamoyls, acyloxys, acylaminos, aroylaminos, and combinations thereof.

More particular non-limiting examples of alkyl substituents R associated with formula (I) through (V) include methyl, ethyl, propyl, butyl, pentyl, hexyl, cyclopentyl, cyclohexyl, benzyl, phenyl, methylphenyl, and tert-butylphenyl groups and the like, including all their isomers, for example tertiary-butyl, isopropyl, and the like. Other possible radicals include substituted alkyls and aryls such as, for example, fluoromethyl, fluroethyl, difluroethyl, iodopropyl, bromohexyl, chlorobenzyl and hydrocarbyl substituted organometalloid radicals including trimethylsilyl, trimethylgermyl, methyldiethylsilyl and the like; and halocarbyl-substituted organometalloid radicals including tris(trifluoromethyl)silyl, methylbis(difluoromethyl)silyl, bromomethyldimethylgermyl and the like; and disubstituted boron radicals including dimethylboron for example; and disubstituted Group 15 radicals including dimethylamine, dimethylphosphine, diphenylamine, methylphenylphosphine, Group 16 radicals including methoxy, ethoxy, propoxy, phenoxy, methylsulfide and ethylsulfide. Other substituents R include olefins such as but not limited to olefinically unsaturated substituents including vinyl-terminated ligands, for example 3-butenyl, 2-propenyl, 5-hexenyl and the like. In one embodiment, at least two R groups, two adjacent R groups in one embodiment, are joined to form a ring structure having from 3 to 30 atoms selected from the group consisting of carbon, nitrogen, oxygen, phosphorous, silicon, germanium, aluminum, boron and combinations thereof. Also, a substituent group R group such as 1-butanyl may form a bonding association to the element M.

Each X in the formula (I) above and for the formulas/structures (II) through (V) below is independently selected from the group consisting of: any leaving group in one embodiment; halogen ions, hydrides, $C_1$ to $C_{12}$ alkyls, $C_2$ to $C_{12}$ alkenyls, $C_6$ to $C_{12}$ aryls, $C_7$ to $C_{20}$ alkylaryls, $C_1$ to $C_{12}$ alkoxys, $C_6$ to $C_{16}$ aryloxys, $C_7$ to $C_{18}$ alkylaryloxys, $C_1$ to $C_{12}$ fluoroalkyls, $C_6$ to $C_{12}$ fluoroaryls, and $C_1$ to $C_{12}$ heteroatom-containing hydrocarbons and substituted derivatives thereof in a more particular embodiment; hydride, halogen ions, $C_1$ to $C_6$ alkyls, $C_2$ to $C_6$ alkenyls, $C_7$ to $C_{18}$ alkylaryls, $C_1$ to $C_6$ alkoxys, $C_6$ to $C_{14}$ aryloxys, $C_7$ to $C_{16}$ alkylaryloxys, $C_1$ to $C_6$ alkylcarboxylates, $C_1$ to $C_6$ fluorinated alkylcarboxylates, $C_6$ to $C_{12}$ arylcarboxylates, $C_7$ to $C_{18}$ alkylarylcarboxylates, $C_1$ to $C_6$ fluoroalkyls, $C_2$ to $C_6$ fluoroalkenyls, and $C_7$ to $C_{18}$ fluoroalkylaryls in yet a more particular embodiment; hydride, chloride, fluoride, methyl, phenyl, phenoxy, benzoxy, tosyl, fluoromethyls and fluorophenyls in yet a more particular embodiment; $C_1$ to $C_{12}$ alkyls, $C_2$ to $C_{12}$ alkenyls, $C_6$ to $C_{12}$ aryls, $C_7$ to $C_{20}$ alkylaryls, substituted $C_1$ to $C_{12}$ alkyls, substituted $C_6$ to $C_{12}$ aryls, substituted $C_7$ to $C_{20}$ alkylaryls and $C_1$ to $C_{12}$ heteroatom-containing alkyls, $C_1$ to $C_{12}$ heteroatom-containing aryls and $C_1$ to $C_{12}$ heteroatom-containing alkylaryls in yet a more particular embodiment; chloride, fluoride, $C_1$ to $C_6$ alkyls, $C_2$ to $C_6$ alkenyls, $C_7$ to $C_{18}$ alkylaryls, halogenated $C_1$ to $C_6$ alkyls, halogenated $C_2$ to $C_6$ alkenyls, and halogenated $C_7$ to $C_{18}$ alkylaryls in yet a more particular embodiment; fluoride, methyl, ethyl, propyl, phenyl, methylphenyl, dimethylphenyl, trimethylphenyl, fluoromethyls (mono-, di- and trifluoromethyls) and fluorophenyls (mono-, di-, tri-, tetra- and pentafluorophenyls) in yet a more particular embodiment; and fluoride in yet a more particular embodiment.

Other non-limiting examples of X groups in formula (I) include amines, phosphines, ethers, carboxylates, dienes, hydrocarbon radicals having from 1 to 20 carbon atoms, fluorinated hydrocarbon radicals (e.g., —$C_6F_5$ (pentafluorophenyl)), fluorinated alkylcarboxylates (e.g., $CF_3C(O)O^-$), hydrides and halogen ions and combinations thereof. Other examples of X ligands include alkyl groups such as cyclobutyl, cyclohexyl, methyl, heptyl, tolyl, trifluoromethyl, tetramethylene, pentamethylene, methylidene, methyoxy, ethyoxy, propoxy, phenoxy, bis(N-methylanilide), dimethylamide, dimethylphosphide radicals and the like. In one embodiment, two or more X's form a part of a fused ring or ring system.

In another aspect of the invention, the metallocene catalyst component includes those of formula (I) where $Cp^A$ and $Cp^B$ are bridged to each other by at least one bridging group, (A), such that the structure is represented by formula (II):

$$Cp^A(A)Cp^BMX_n \qquad (II)$$

These bridged compounds represented by formula (II) are known as "bridged metallocenes". $Cp^A$, $Cp^B$, M, X and n in structure (II) are as defined above for formula (I); and wherein each Cp ligand is chemically bonded to M, and (A) is chemically bonded to each Cp. Non-limiting examples of bridging group (A) include divalent hydrocarbon groups containing at least one Group 13 to 16 atom, such as but not limited to at least one of a carbon, oxygen, nitrogen, silicon, aluminum, boron, germanium and tin atom and combinations thereof; wherein the heteroatom may also be $C_1$ to $C_{12}$ alkyl or aryl substituted to satisfy neutral valency. The bridging group (A) may also contain substituent groups R as defined above (for formula (I)) including halogen radicals and iron. More particular non-limiting examples of bridging group (A) are represented by $C_1$ to $C_6$ alkylenes, substituted $C_1$ to $C_6$ alkylenes, oxygen, sulfur, R'$_2$C=, R'$_2$Si=, —Si(R')$_2$Si(R'$_2$)—, R'$_2$Ge=, R'P= (wherein "=" represents two chemical bonds), where R' is independently selected from the group consisting of hydride, hydrocarbyl, substituted hydrocarbyl, halocarbyl, substituted halocarbyl, hydrocarbyl-substituted organometalloid, halocarbyl-substituted organometalloid, disubstituted boron, disubstituted Group 15 atoms, substituted Group 16 atoms, and halogen radical; and wherein two or more R' may be joined to form a ring or ring system. In one embodiment, the bridged metallocene catalyst component of formula (II) has two or more bridging groups (A).

Other non-limiting examples of bridging group (A) include methylene, ethylene, ethylidene, propylidene, isopropylidene, diphenylmethylene, 1,2-dimethylethylene, 1,2-diphenylethylene, 1,1,2,2-tetramethylethylene, dimethylsilyl, diethylsilyl, methyl-ethylsilyl, trifluoromethylbutylsilyl, bis(trifluoromethyl)silyl, di(n-butyl)silyl, di(n-propyl)silyl, di(i-propyl)silyl, di(n-hexyl)silyl, dicyclohexylsilyl, diphenylsilyl, cyclohexylphenylsilyl, t-butylcyclohexylsilyl, di(t-butylphenyl)silyl, di(p-tolyl)silyl and the corresponding moieties wherein the Si atom is replaced by a Ge or a C atom; dimethylsilyl, diethylsilyl, dimethylgermyl and diethylgermyl.

In another embodiment, bridging group (A) may also be cyclic, comprising, for example 4 to 10, 5 to 7 ring members in a more particular embodiment. The ring members may be selected from the group consisting of the elements mentioned above, and from one or more of B, C, Si, Ge, N and O in a particular embodiment. Non-limiting examples of ring structures which may be present as or part of the bridging moiety are cyclobutylidene, cyclopentylidene, cyclohexylidene, cycloheptylidene, cyclooctylidene and the corresponding rings where one or two carbon atoms are replaced by at least one of Si, Ge, N and O, in particular, Si and Ge. The bonding arrangement between the ring and the Cp groups may be either cis-, trans-, or a combination.

The cyclic bridging groups (A) may be saturated or unsaturated and/or carry one or more substituents and/or be fused to one or more other ring structures. If present, the one or more substituents are selected from the group consisting of hydrocarbyl (e.g., alkyl such as methyl) and halogen (e.g., F, Cl) in one embodiment. The one or more Cp groups which the above cyclic bridging moieties may optionally be fused to may be saturated or unsaturated and are selected from the group consisting of those having 4 to 10, more particularly 5, 6 or 7 ring members (selected from the group consisting of C, N, O and S in a particular embodiment) such as, for example, cyclopentyl, cyclohexyl and phenyl. Moreover, these ring structures may themselves be fused such as, for example, in the case of a naphthyl group. Moreover, these (optionally fused) ring structures may carry one or more substituents. Illustrative, non-limiting examples of these substituents are hydrocarbyl (particularly alkyl) groups and halogen atoms.

The ligands $Cp^A$ and $Cp^B$ of formulae (I) and (II) are different from each other in one embodiment, and the same in another embodiment.

In yet another aspect of the invention, the metallocene catalyst components include bridged mono-ligand metallocene compounds (e.g., mono cyclopentadienyl catalyst components). In this embodiment, the at least one metallocene catalyst component is a bridged "half-sandwich" metallocene represented by the formula (III):

$$Cp^A(A)QMX_n \qquad (III)$$

wherein $Cp^A$ is defined above and is bound to M; (A) is a bridging group bonded to Q and $Cp^A$; and wherein an atom from the Q group is bonded to M; and n is an integer 0, 1 or 2. In formula (III) above, $Cp^A$, (A) and Q may form a fused ring system. The X groups and n of formula (III) are as defined above in formula (I) and (II). In one embodiment, $Cp^A$ is selected from the group consisting of cyclopentadienyl, indenyl, tetrahydroindenyl, fluorenyl, substituted versions thereof, and combinations thereof.

In formula (III), Q is a heteroatom-containing ligand in which the bonding atom (the atom that is bonded with the metal M) is selected from the group consisting of Group 15 atoms and Group 16 atoms in one embodiment, and selected from the group consisting of nitrogen, phosphorus, oxygen or sulfur atom in a more particular embodiment, and nitrogen and oxygen in yet a more particular embodiment. Non-limiting examples of Q groups include alkylamines, arylamines, mercapto compounds, ethoxy compounds, carboxylates (e.g., pivalate), carbamates, azenyl, azulene, pentalene, phosphoyl, phosphinimine, pyrrolyl, pyrozolyl, carbazolyl, borabenzene other compounds comprising Group 15 and Group 16 atoms capable of bonding with M.

In yet another aspect of the invention, the at least one metallocene catalyst component is an unbridged "half sandwich" metallocene represented by the formula (IVa):

$$Cp^AMQ_qX_n \qquad (IVa)$$

wherein $Cp^A$ is defined as for the Cp groups in (I) and is a ligand that is bonded to M; each Q is independently bonded to M; X is a leaving group as described above in (I); n ranges from 0 to 3, and is 0 or 3 in one embodiment; q ranges from 0 to 3, and is 0 or 3 in one embodiment. In one embodiment, $Cp^A$ is selected from the group consisting of cyclopentadienyl, indenyl, tetrahydroindenyl, fluorenyl, substituted version thereof, and combinations thereof.

In formula (IVa), Q is selected from the group consisting of $ROO^-$, RO—, R(O)—, —NR—, —$CR_2$—, —S—, —$NR_2$, —$CR_3$, —SR, —$SiR_3$, —$PR_2$, —H, and substituted and unsubstituted aryl groups, wherein R is selected from the group consisting of $C_1$ to $C_6$ alkyls, $C_6$ to $C_{12}$ aryls, $C_1$ to $C_6$ alkylamines, $C_6$ to $C_{12}$ alkylarylamines, $C_1$ to $C_6$ alkoxys, $C_6$ to $C_{12}$ aryloxys, and the like. Non-limiting examples of Q include $C_1$ to $C_{12}$ carbamates, $C_1$ to $C_{12}$ carboxylates (e.g., pivalate), $C_2$ to $C_{20}$ allyls, and $C_2$ to $C_{20}$ heteroallyl moieties.

Described another way, the "half sandwich" metallocenes above can be described as in formula (IVb), such as described in, for example, U.S. Pat. No. 6,069,213:

$$Cp^A M(Q_2 GZ)X_n \text{ or}$$

$$T(Cp^A M(Q_2 GZ)X_n)_m \quad \text{(IVb)}$$

wherein M, $Cp^A$, X and n are as defined above;

$Q_2GZ$ forms a polydentate ligand unit (e.g., pivalate), wherein at least one of the Q groups form a bond with M, and is defined such that each Q is independently selected from the group consisting of —O—, —NR—, —$CR_2$— and —S—; G is either carbon or silicon; and Z is selected from the group consisting of R, —OR, —$NR_2$, —$CR_3$, —SR, —$SiR_3$, —$PR_2$, and hydride, providing that when Q is —NR—, then Z is selected from the group consisting of —OR, —$NR_2$, —SR, —$SiR_3$, —$PR_2$; and provided that neutral valency for Q is satisfied by Z; and wherein each R is independently selected from the group consisting of $C_1$ to $C_{10}$ heteroatom containing groups, $C_1$ to $C_{10}$ alkyls, $C_6$ to $C_{12}$ aryls, $C_6$ to $C_{12}$ alkylaryls, $C_1$ to $C_{10}$ alkoxys, and $C_6$ to $C_{12}$ aryloxys;

n is 1 or 2 in a particular embodiment; and

T is a bridging group selected from the group consisting of $C_1$ to $C_{10}$ alkylenes, $C_6$ to $C_{12}$ arylenes and $C_1$ to $C_{10}$ heteroatom containing groups, and $C_6$ to $C_{12}$ heterocyclic groups; wherein each T group bridges adjacent "$Cp^A M (Q_2GZ)X_n$" groups, and is chemically bonded to the $Cp^A$ groups.

m is an integer from 1 to 7; m is an integer from 2 to 6 in a more particular embodiment.

In another aspect of the invention, the at least one metallocene catalyst component can be described more particularly in structures (Va), (Vb), (Vc) and (Vd):

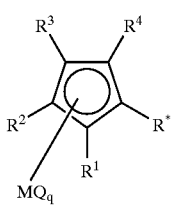

(Va-i)

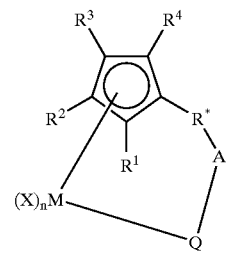

(Va-ii)

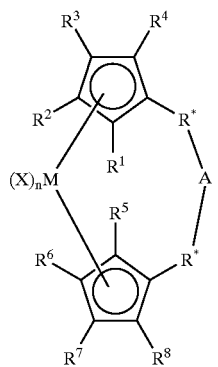

(Vb)

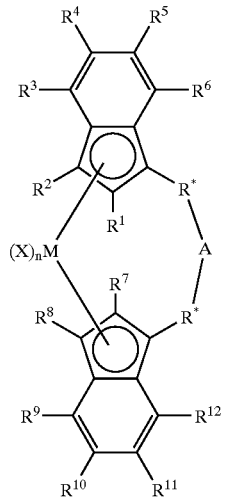

(Vc)

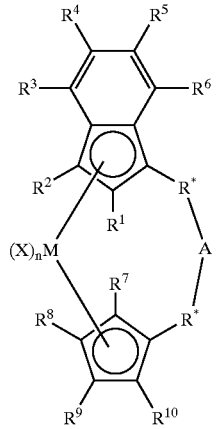

(Vd)

wherein in structures (Va) to (Vd) M is selected from the group consisting of Group 3 to Group 12 atoms, and selected from the group consisting of Group 3 to Group 10 atoms in a more particular embodiment, and selected from the group consisting of Group 3 to Group 6 atoms in yet a more particular embodiment, and selected from the group consisting of Group 4 atoms in yet a more particular embodiment, and selected from the group consisting of Zr and Hf in yet a more particular embodiment; and is Zr in yet a more particular embodiment;

wherein Q in (Va-i) and (Va-ii) is selected from the group consisting of halogen ions, alkyls, alkylenes, aryls, arylenes, alkoxys, aryloxys, amines, alkylamines, phosphines, alkylphosphines, substituted alkyls, substituted aryls, substituted alkoxys, substituted aryloxys, substituted amines, substituted alkylamines, substituted phosphines, substituted alkylphosphines, carbamates, heteroallyls, carboxylates (non-limiting examples of suitable carbamates and carboxylates include trimethylacetate, trimethylacetate, methylacetate, p-toluate, benzoate, diethylcarbamate, and dimethylcarbamate), fluorinated alkyls, fluorinated aryls, and fluorinated alkylcarboxylates;

q is an integer ranging from 1 to 3;

wherein each R* is independently: selected from the group consisting of hydrocarbyls and heteroatom-containing hydrocarbyls in one embodiment; and selected from the group consisting of alkylenes, substituted alkylenes and heteroatom-containing hydrocarbyls in another embodiment; and selected from the group consisting of $C_1$ to $C_{12}$ alkylenes, $C_1$ to $C_{12}$ substituted alkylenes, and $C_1$ to $C_{12}$ heteroatom-containing hydrocarbons in a more particular embodiment; and selected from the group consisting of $C_1$ to $C_4$ alkylenes in yet a more particular embodiment; and wherein both R* groups are identical in another embodiment in structures (Vb-d);

A is as described above for (A) in structure (II), and more particularly, selected from the group consisting of —O—, —S—, —SO$_2$—, —NR—, =SiR$_2$, =GeR$_2$, =SnR$_2$, —R$_2$SiSiR$_2$—, RP=, $C_1$ to $C_{12}$ alkylenes, substituted $C_1$ to $C_{12}$ alkylenes, divalent $C_4$ to $C_{12}$ cyclic hydrocarbons and substituted and unsubstituted aryl groups in one embodiment; and selected from the group consisting of $C_5$ to $C_8$ cyclic hydrocarbons, —CH$_2$CH$_2$—, =CR$_2$ and =SiR$_2$ in a more particular embodiment; wherein and R is selected from the group consisting of alkyls, cycloalkyls, aryls, alkoxys, fluoroalkyls and heteroatom-containing hydrocarbons in one embodiment; and R is selected from the group consisting of $C_1$ to $C_6$ alkyls, substituted phenyls, phenyl, and $C_1$ to $C_6$ alkoxys in a more particular embodiment; and R is selected from the group consisting of methoxy, methyl, phenoxy, and phenyl in yet a more particular embodiment;

wherein A may be absent in yet another embodiment, in which case each R* is defined as for $R^1$–$R^{12}$;

each X is as described above in (I);

n is an integer from 0 to 4, and from 1 to 3 in another embodiment, and 1 or 2 in yet another embodiment; and $R^1$ through $R^{12}$ are independently: selected from the group consisting of hydrogen radical, halogen radicals, $C_1$ to $C_{12}$ alkyls, $C_2$ to $C_{12}$ alkenyls, $C_6$ to $C_{12}$ aryls, $C_7$ to $C_{20}$ alkylaryls, $C_1$ to $C_{12}$ alkoxys, $C_1$ to $C_{12}$ fluoroalkyls, $C_6$ to $C_{12}$ fluoroaryls, and $C_1$ to $C_{12}$ heteroatom-containing hydrocarbons and substituted derivatives thereof in one embodiment; selected from the group consisting of hydrogen radical, fluorine radical, chlorine radical, bromine radical, $C_1$ to $C_6$ alkyls, $C_2$ to $C_6$ alkenyls, $C_7$ to $Cl_8$ alkylaryls, $C_1$ to $C_6$ fluoroalkyls, $C_2$ to $C_6$ fluoroalkenyls, $C_7$ to $C_{18}$ fluoroalkylaryls in a more particular embodiment; and hydrogen radical, fluorine radical, chlorine radical, methyl, ethyl, propyl, isopropyl, butyl, isobutyl, tertiary butyl, hexyl, phenyl, 2,6-di-methylpheyl, and 4-tertiarybutylpheyl groups in yet a more particular embodiment; wherein adjacent R groups may form a ring, either saturated, partially saturated, or completely saturated.

The structure of the metallocene catalyst component represented by (Va) may take on many forms such as disclosed in, for example, U.S. Pat. No. 5,026,798, U.S. Pat. No. 5,703,187, and U.S. Pat. No. 5,747,406, including a dimer or oligomeric structure, such as disclosed in, for example, U.S. Pat. No. 5,026,798 and U.S. Pat. No. 6,069,213.

In a particular embodiment of the metallocene represented in (Vd), $R^1$ and $R^2$ form a conjugated 6-membered carbon ring system that may or may not be substituted.

Non-limiting examples of metallocene catalyst components consistent with the description herein include:

cyclopentadienylzirconium $X_n$,
indenylzirconium $X_n$,
(1-methylindenyl)zirconium $X_n$,
(2-methylindenyl)zirconium $X_n$,
(1-propylindenyl)zirconium $X_n$,
(2-propylindenyl)zirconium $X_n$,
(1-butylindenyl)zirconium $X_n$,
(2-butylindenyl)zirconium $X_n$,
(methylcyclopentadienyl)zirconium $X_n$,
tetrahydroindenylzirconium $X_n$,
(pentamethylcyclopentadienyl)zirconium $X_n$,
cyclopentadienylzirconium $X_n$,
pentamethylcyclopentadienyltitanium $X_n$,
tetramethylcyclopentyltitanium $X_n$,
1,2,4-trimethylcyclopentadienylzirconium $X_n$,
dimethylsilyl(1,2,3,4-tetramethylcyclopentadienyl)(cyclopentadienyl)zirconium $X_n$,
dimethylsilyl(1,2,3,4-tetramethylcyclopentadienyl)(1,2,3-trimethyl-cyclopentadienyl)zirconium $X_n$,
dimethylsilyl(1,2,3,4-tetramethylcyclopentadienyl)(1,2-dimethyl-cyclopentadienyl)zirconium $X_n$,
dimethylsilyl(1,2,3,4-tetramethyl-cyclopentadienyl)(2-methylcyclopentadienyl)zirconium $X_n$,
dimethylsilyl(cyclopentadienyl)(indenyl)zirconium $X_n$,
dimethylsilyl(2-methylindenyl)(fluorenyl)zirconium $X_n$,
diphenylsilyl(1,2,3,4-tetramethyl-cyclopentadienyl)(3-propylcyclopentadienyl)zirconium $X_n$,
dimethylsilyl (1,2,3,4-tetramethylcyclopentadienyl) (3-t-butylcyclopentadienyl)zirconium $X_n$,
dimethylgermyl(1,2-dimethylcyclopentadienyl)(3-isopropylcyclopentadienyl)zirconium $X_n$,
dimethylsilyl(1,2,3,4-tetramethyl-cyclopentadienyl)(3-methylcyclopentadienyl) zirconium $X_n$,
diphenylmethylidene(cyclopentadienyl)(9-fluorenyl) zirconium $X_n$,
diphenylmethylidene(cyclopentadienyl)(indenyl)zirconium $X_n$,
iso-propylidenebis(cyclopentadienyl)zirconium $X_n$,
iso-propylidene(cyclopentadienyl)(9-fluorenyl)zirconium $X_n$,
iso-propylidene(3-methylcyclopentadienyl)(9-fluorenyl) zirconium $X_n$,
ethylenebis(9-fluorenyl)zirconium $X_n$,
meso-ethylenebis(1-indenyl)zirconium $X_n$,
ethylenebis(1-indenyl)zirconium $X_n$,
ethylenebis(2-methyl-1-indenyl)zirconium $X_n$,
ethylenebis(2-methyl-4,5,6,7-tetrahydro-1-indenyl) zirconium $X_n$,
ethylenebis(2-propyl-4,5,6,7-tetrahydro-1-indenyl) zirconium $X_n$, ethylenebis(2-isopropyl-4,5,6,7-tetrahydro-1-indenyl) zirconium $X_n$,
ethylenebis(2-butyl-4,5,6,7-tetrahydro-1-indenyl)zirconium $X_n$,
ethylenebis(2-isobutyl-4,5,6,7-tetrahydro-1-indenyl) zirconium $X_n$,
dimethylsilyl(4,5,6,7-tetrahydro-1-indenyl)zirconium $X_n$,
diphenyl(4,5,6,7-tetrahydro-1-indenyl)zirconium $X_n$,
ethylenebis(4,5,6,7-tetrahydro-1-indenyl)zirconium $X_n$,
dimethylsilylbis(cyclopentadienyl)zirconium $X_n$,
dimethylsilylbis(9-fluorenyl)zirconium $X_n$,
dimethylsilylbis(1-indenyl)zirconium $X_n$,
dimethylsilylbis(2-methylindenyl)zirconium $X_n$,
dimethylsilylbis(2-propylindenyl)zirconium $X_n$,
dimethylsilylbis(2-butylindenyl)zirconium $X_n$,
diphenylsilylbis(2-methylindenyl)zirconium $X_n$,
diphenylsilylbis(2-propylindenyl)zirconium $X_n$,
diphenylsilylbis(2-butylindenyl)zirconium $X_n$,
dimethylgermylbis(2-methylindenyl)zirconium $X_n$
dimethylsilylbis(tetrahydroindenyl)zirconium $X_n$,
dimethylsilylbis(tetramethylcyclopentadienyl)zirconium $X_n$,
dimethylsilyl(cyclopentadienyl)(9-fluorenyl)zirconium $X_n$,
diphenylsilyl(cyclopentadienyl)(9-fluorenyl)zirconium $X_n$,
diphenylsilylbis(indenyl)zirconium $X_n$,
cyclotrimethylenesilyl(tetramethylcyclopentadienyl) (cyclopentadienyl)zirconium $X_n$,
cyclotetramethylenesilyl(tetramethylcyclopentadienyl) (cyclopentadienyl) zirconium $X_n$,
cyclotrimethylenesilyl(tetramethylcyclopentadienyl)(2-methylindenyl)zirconium $X_n$,
cyclotrimethylenesilyl(tetramethylcyclopentadienyl)(3-methylcyclopentadienyl)zirconium $X_n$,
cyclotrimethylenesilylbis(2-methylindenyl)zirconium $X_n$,
cyclotrimethylenesilyl(tetramethylcyclopentadienyl)(2,3,5-trimethylcyclopentadienyl)zirconium $X_n$,
cyclotrimethylenesilylbis(tetramethylcyclopentadienyl) zirconium $X_n$,
dimethylsilyl(tetramethylcyclopentadieneyl)(N-tert-butylamido)titanium $X_n$,
bis(cyclopentadienyl)chromium $X_n$,
bis(cyclopentadienyl)zirconium $X_n$,
bis(n-butylcyclopentadienyl)zirconium $X_n$,
bis(n-dodecylcyclopentadienyl)zirconium $X_n$,
bis(ethylcyclopentadienyl)zirconium $X_n$,
bis(iso-butylcyclopentadienyl)zirconium $X_n$,
bis(iso-propylcyclopentadienyl)zirconium $X_n$,
bis(methylcyclopentadienyl)zirconium $X_n$,
bis(n-oxtylcyclopentadienyl)zirconium $X_n$,
bis(n-pentylcyclopentadienyl)zirconium $X_n$,
bis(n-propylcyclopentadienyl)zirconium $X_n$,
bis(trimethylsilylcyclopentadienyl)zirconium $X_n$,
bis(1,3-bis(trimethylsilyl)cyclopentadienyl)zirconium $X_n$,
bis(1-ethyl-2-methylcyclopentadienyl)zirconium $X_n$,
bis(1-ethyl-3-methylcyclopentadienyl)zirconium $X_n$,
bis(pentamethylcyclopentadienyl)zirconium $X_n$,
bis(pentamethylcyclopentadienyl)zirconium $X_n$,
bis(1-propyl-3-methylcyclopentadienyl)zirconium $X_n$,
bis(1-n-butyl-3-methylcyclopentadienyl)zirconium $X_n$,
bis(1-isobutyl-3-methylcyclopentadienyl)zirconium $X_n$,
bis(1-propyl-3-butylcyclopentadienyl)zirconium $X_n$,
bis(1,3-n-butylcyclopentadienyl)zirconium $X_n$,
bis(4,7-dimethylindenyl)zirconium $X_n$,
bis(indenyl)zirconium $X_n$,
bis(2-methylindenyl)zirconium $X_n$,
cyclopentadienylindenylzirconium $X_n$,
bis(n-propylcyclopentadienyl)hafnium $X_n$,
bis(n-butylcyclopentadienyl)hafnium $X_n$,
bis(n-pentylcyclopentadienyl)hafnium $X_n$,
(n-propyl cyclopentadienyl)(n-butyl cyclopentadienyl) hafnium $X_n$,
bis[(2-trimethylsilylethyl)cyclopentadienyl]hafnium $X_n$,
bis(trimethylsilyl cyclopentadienyl)hafnium $X_n$,
bis(2-n-propylindenyl)hafnium $X_n$,
bis(2-n-butylindenyl)hafnium $X_n$,
dimethylsilylbis(n-propylcyclopentadienyl)hafnium $X_n$,
dimethylsilylbis(n-butylcyclopentadienyl)hafnium $X_n$,
bis(9-n-propylfluorenyl)hafnium $X_n$,
bis(9-n-butylfluorenyl)hafnium $X_n$,
(9-n-propylfluorenyl)(2-n-propylindenyl)hafnium $X_n$,
bis(1-n-propyl-2-methylcyclopentadienyl)hafnium $X_n$,
(n-propylcyclopentadienyl)(1-n-propyl-3-n-butylcyclopentadienyl)hafnium $X_n$,
dimethylsilyl(tetramethylcyclopentadienyl) (cyclopropylamido)titanium $X_n$,
dimethylsilyl(tetramethyleyclopentadienyl) (cyclobutylamido)titanium $X_n$,
dimethylsilyl(tetramethyleyclopentadienyl) (cyclopentylamido)titanium $X_n$,
dimethylsilyl(tetramethylcyclopentadienyl) (cyclohexylamido)titanium $X_n$,
dimethylsilyl(tetramethylcyclopentadienyl) (cycloheptylamido)titanium $X_n$,
dimethylsilyl(tetramethylcyclopentadienyl) (cyclooctylamido)titanium $X_n$,
dimethylsilyl(tetramethylcyclopentadienyl) (cyclononylamido)titanium $X_n$,
dimethylsilyl(tetramethylcyclopentadienyl) (cyclodecylamido)titanium $X_n$,
dimethylsilyl(tetramethylcyclopentadienyl) (cycloundecylamido)titanium $X_n$,
dimethylsilyl(tetramethylcyclopentadienyl) (cyclododecylamido)titanium $X_n$,
dimethylsilyl(tetramethylcyclopentadienyl)(sec-butylamido)titanium $X_n$,
dimethylsilyl(tetramethylcyclopentadienyl)(n-octylamido) titanium $X_n$,
dimethylsilyl(tetramethylcyclopentadienyl)(n-decylamido) titanium $X_n$,
dimethylsilyl(tetramethylcyclopentadienyl)(n-octadecylamido)titanium $X_n$,
methylphenylsilyl(tetramethylcyclopentadienyl) (cyclopropylamido)titanium $X_n$,
methylphenylsilyl(tetramethylcyclopentadienyl) (cyclobutylamido)titanium $X_n$,
methylphenylsilyl(tetramethylcyclopentadienyl) (cyclopentylamido)titanium $X_n$,
methylphenylsilyl(tetramethylcyclopentadienyl) (cyclohexylamido)titanium $X_n$,
methylphenylsilyl(tetramethylcyclopentadienyl) (cycloheptylamido)titanium $X_n$,
methylphenylsilyl(tetramethylcyclopentadienyl) (cyclooctylamido)titanium $X_n$,
methylphenylsilyl(tetramethylcyclopentadienyl) (cyclononylamido)titanium $X_n$,
methylphenylsilyl(tetramethylcyclopentadienyl) (cyclodecylamido)titanium, $X_n$,
methylphenylsilyl(tetramethylcyclopentadienyl) (cycloundecylamido)titanium $X_n$,
methylphenylsilyl(tetramethylcyclopentadienyl) (cyclododecylamido)titanium $X_n$,
methylphenylsilyl(tetramethylcyclopentadienyl)(sec-butylamido)titanium $X_n$,
methylphenylsilyl(tetramethylcyclopentadienyl)(n-octylamido)titanium $X_n$, methylphenylsilyl(tetramethylcyclopentadienyl)(n-decylamido)titanium $X_n$,
methylphenylsilyl(tetramethylcyclopentadienyl)(n-octadecylamido)titanium $X_n$,
diphenylsilyl(tetramethylcyclopentadienyl)(cyclopropylamido)titanium $X_n$,
diphenylsilyl(tetramethylcyclopentadienyl)(cyclobutylamido)titanium $X_n$,
diphenylsilyl(tetramethylcyclopentadienyl)(cyclopentylamido)titanium $X_n$,
diphenylsilyl(tetramethylcyclopentadienyl)(cyclohexylamido)titanium $X_n$,
diphenylsilyl(tetramethylcyclopentadienyl)(cycloheptylamido)titanium $X_n$,
diphenylsilyl(tetramethylcyclopentadienyl)(cyclooctylamido)titanium $X_n$,
diphenylsilyl(tetramethylcyclopentadienyl)(cyclononylamido)titanium $X_n$,
diphenylsilyl(tetramethylcyclopentadienyl)(cyclodecylamido)titanium $X_n$,
diphenylsilyl(tetramethylcyclopentadienyl)(cycloundecylamido)titanium $X_n$,
diphenylsilyl(tetramethylcyclopentadienyl)(cyclododecylamido)titanium $X_n$,
diphenylsilyl(tetramethylcyclopentadienyl)(sec-butylamido)titanium $X_n$,
diphenylsilyl(tetramethyleyclopentadienyl)(n-octylamido)titanium $X_n$,
diphenylsilyl(tetramethyleyclopentadienyl)(n-decylamido)titanium $X_n$,
diphenylsilyl(tetramethylcyclopentadienyl)(n-octadecylamido)titanium $X_n$, and derivatives thereof.

Wherein the value of n is 1, 2 or 3, and at least one X is a fluoride ion. By "derivatives thereof", it is meant any substitution or ring formation as described above for structures (Va-d) in one embodiment; and in particular, replacement of the metal "M" (Cr, Zr, Ti or Hf) with an atom selected from the group consisting of Cr, Zr, Hf and Ti; and replacement of the "X" group with any of $C_1$ to $C_5$ alkyls, $C_6$ aryls, $C_6$ to $C_{10}$ alkylaryls, fluorine, chlorine, or bromine. In a particular embodiment, each of the above metallocenes is a fluorided metallocene wherein one or more of the X groups is a fluoride; and all X groups are fluorides in yet a more particular embodiment.

More particularly, non-limiting examples of the fluorided catalyst components useful in the method of the invention are as follows:
Bis(methylcyclopentadienyl)zirconium difluoride,
Bis(ethylcyclopentadienyl)zirconium difluoride,
Bis(propylcyclopentadienyl)zirconium difluoride,
Bis(isopropylcyclopentadienyl)zirconium difluoride,
Bis(butylcyclopentadienyl)zirconium difluoride,
Bis(isobutylcyclopentadienyl)zirconium difluoride,
Bis(neopentylcyclopentadienyl)zirconium difluoride,
Bis(cyclopentylcyclopentadienyl)zirconium difluoride,
Bis(cyclohexylmethyleyclopentadienyl)zirconium difluoride,
Bis(allylcyclopentadienyl)zirconium difluoride,
Bis((3-butenyl)cyclopentadienyl)zirconium difluoride,
Bis(trimethylsilylcyclopentadienyl)zirconium difluoride,
Bis(trimethylgermylcyclopentadienyl)zirconium difluoride,
Bis(trimethylsilylmethylcyclopentadienyl)zirconium difluoride,
Bis(1,2-dimethylcyclopentadienyl)zirconium difluoride,
Bis(1,3-dimethylcyclopentadienyl)zirconium difluoride,
Bis(1,2,3-trimethylcyclopentadienyl)zirconium difluoride,
Bis(1,2,4-trimethylcyclopentadienyl)zirconium difluoride,
Bis(tetramethylcyclopentadienyl)zirconium difluoride,
Bis(1,3-methylethylcyclopentadienyl)zirconium difluoride,
Bis(1,3-methylpropylcyclopentadienyl)zirconium difluoride,
Bis(1,3-methylbutylcyclopentadienyl)zirconium difluoride,
Bis(phenylcyclopentadienyl)zirconium difluoride,
Bis(1,3-methylphenylcyclopentadienyl)zirconium difluoride,
Bis(benzylcyclopentadienyl)zirconium difluoride,
Bis(1,3-methylbenzylcyclopentadienyl)zirconium difluoride,
Bis(phenethylcyclopentadienyl)zirconium difluoride,
Bis((3-phenylpropyl)cyclopentadienyl)zirconium difluoride,
(Tetramethylcylopentadienyl)(propylcyclopentadienyl)zirconium difluoride,
(Pentamethylcylopentadienyl)(propylcyclopentadienyl)zirconium difluoride,
Cyclopentadienyl(propylcyclopentadienyl)zirconium difluoride,
Cyclopentadienyl(butylcyclopentadienyl)zirconium difluoride,
Cyclopentadienyl(cyclopentylcyclopentadienyl)zirconium difluoride,
Cyclopentadienyl (tetrahydroindenyl)zirconium difluoride,
Cyclopentadienyl(1,3-methylbutylcyclopentadienyl)zirconium difluoride,
Cyclopentadienyl(tetramethylcyclopentadienyl)zirconium difluoride,
Cyclopentadienyl(propyltetramethylcyclopentadienyl)zirconium difluoride,
Cyclopentadienyl(butyltetramethylcyclopentadienyl)zirconium difluoride,
Cyclopentadienyl(cyclopentyltetramethylcyclopentadienyl)zirconium difluoride,
Cyclopentadienyl(indenyl)zirconium difluoride,
Cyclopentadienyl(1-methylindenyl)zirconium difluoride,
Cyclopentadienyl(fluorenyl)zirconium difluoride,
Cyclopentadienyl(tetrahydrofluorenyl)zirconium difluoride,
Cyclopentadienyl(octahydrofluorenyl)zirconium difluoride,
Bis(tetrahydroindenyl)zirconium difluoride,
Bis(trihydropentalenyl)zirconium difluoride,
Bis(pentahydroazulenyl)zirconium difluoride,
Dimethylsilylbis(tetrahydroindenyl)zirconium difluoride,
Ethylenebis(tetrahydroindenyl)zirconium difluoride,
Bis(indenyl)zirconium difluoride,
Bis(1-methylindenyl)zirconium difluoride,
Bis(2-methylindenyl)zirconium difluoride,
Bis(4,7-dimethylindenyl)zirconium difluoride,
Bis(5,6-dimethylindenyl)zirconium difluoride,
Bis(1-phenylindenyl)zirconium difluoride,
Bis(2-phenylindenyl)zirconium difluoride,
Bis(fluorenyl)zirconium difluoride,
Bis(1-methylfluorenyl)zirconium difluoride,
Bis(2,7-di-t-butylfluorenyl)zirconium difluoride,
Dimethylsilylbis(3-methylcyclopentadienyl)zirconium difluoride,
Dimethylsilylbis(3-propylcyclopentadienyl)zirconium difluoride,
Dimethylsilylbis(2,4-dimethylcyclopentadienyl)zirconium difluoride,
Dimethylsilylbis(2,3,5-trimethylcyclopentadienyl)zirconium difluoride,
Dimethylsilylbis(tetramethylcyclopentadienyl)zirconium difluoride,
Dimethylsilylbis(indenyl)zirconium difluoride,
Dimethylsilylbis(2-methylindenyl)zirconium difluoride, Dimethylsilylbis(2-methyl-4-phenylindenyl)zirconium difluoride,
Dimethylsilylbis(2-methyl-4-(3,5-di-t-butyl)phenylindenyl) zirconium difluoride,
Dimethylsilylbis(2-methyl-4-naphthylindenyl)zirconium difluoride,
Dimethylsilyl(cyclopentadienyl)(indenyl)zirconium difluoride,
Dimethylsilyl(tetramethylcyclopentadienyl)(indenyl) zirconium difluoride,
Silacyclobutyl(tetramethylcyclopentadienyl)(indenyl) zirconium difluoride,
Silacyclopentyl(tetramethylcyclopentadienyl)(indenyl) zirconium difluoride,
Ethylenebis(indenyl)zirconium difluoride,
Ethylenebis(2-methylindenyl)zirconium difluoride,
Isopropylidene(cyclopentadienyl)(fluorenyl)zirconium difluoride,
Diphenylmethylidene(cyclopentadienyl)(fluorenyl) zirconium difluoride,
Dimethylsilyl(cyclopentadienyl)(fluorenyl)zirconium difluoride,
Diphenylsilyl(cyclopentadienyl)(fluorenyl)zirconium difluoride,
Dimethylsilylbis(fluorenyl)zirconium difluoride,
Ethylenebis(fluorenyl)zirconium difluoride,
Bis(methylcyclopentadienyl)hafnium difluoride,
Bis(ethylcyclopentadienyl)hafnium difluoride,
Bis(propylcyclopentadienyl)hafnium difluoride,
Bis(butylcyclopentadienyl)hafnium difluoride,
Bis(isobutylcyclopentadienyl)hafnium difluoride,
Bis(neopentylcyclopentadienyl)hafnium difluoride,
Bis(cyclopentylcyclopentadienyl)hafnium difluoride,
Bis(allylcyclopentadienyl)hafnium difluoride,
Bis((3-butenyl)cyclopentadienyl)hafnium difluoride,
Bis(cyclohexylmethylcyclopentadienyl)hafnium difluoride,
Bis(trimethylsilylmethylcyclopentadienyl)hafnium difluoride,
Bis((3-phenylpropyl)cyclopentadienyl)hafnium difluoride,
Bis(1,3-methylbutylcyclopentadienyl)hafnium difluoride,
Bis(1,3-methylpropylcyclopentadienyl)hafnium difluoride,
Ethylenebis(indenyl)hafnium difluoride,
Dimethylsilylbis(3-propylcyclopentadienyl)hafnium difluoride,
Dimethylsilylbis(2,4-methylpropylcyclopentadienyl) hafnium difluoride,
Dimethylsilylbis(tetramethylcyclopentadienyl)hafnium difluoride,
Dimethylsilylbis(indenyl)hafnium difluoride,
Diphenylsilylbis(indenyl)hafnium difluoride,
Bis(cyclopentadienyl)titanium difluoride,
Bis(methylcyclopentadienyl)titanium difluoride,
Bis(ethylcyclopentadienyl)titanium difluoride,
Bis(propylcyclopentadienyl)titanium difluoride,
Bis(butylcyclopentadienyl)titanium difluoride,
Bis(isobutylcyclopentadienyl)titanium difluoride,
Bis(neopentylcyclopentadienyl)titanium difluoride,
Bis(cyclopentylcyclopentadienyl)titanium difluoride,
Ethylenebis(indenyl)titanium difluoride,
Dimethylsilylbis(indenyl)titanium difluoride,
Diphenylsilyl(cyclopentadienyl)(fluorenyl)titanium difluoride,
(cyclopentadienyl)zirconium trifluoride,
(indenyl)zirconium trifluoride,
(1-methylindenyl)zirconium trifluoride,
(2-methylindenyl)zirconium trifluoride,
(1-propylindenyl)zirconium trifluoride,
(2-propylindenyl)zirconium trifluoride,
(1-butylindenyl)zirconium trifluoride,
(2-butylindenyl)zirconium trifluoride,
(methylcyclopentadienyl)zirconium trifluoride,
(tetrahydroindenyl)zirconium trifluoride,
(pentamethylcyclopentadienyl)zirconium trifluoride,
(cyclopentadienyl)zirconium trifluoride,
pentamethylcyclopentadienyltitanium trifluoride,
tetramethylcyclopentyldienyltitanium trifluoride,
1,2,4-trimethylcyclopentadienylzirconium trifluoride, and mixtures thereof.

It is contemplated that the metallocene catalysts components described above include their structural or optical or enantiomeric isomers (racemic mixture), and may be a pure enantiomer in one embodiment.

As used herein, a single, bridged, asymmetrically substituted metallocene catalyst component having a racemic and/or meso isomer does not, itself, constitute at least two different bridged, metallocene catalyst components.

The "metallocene catalyst component" useful in the present invention may comprise any combination of any "embodiment" described herein.

When combined to form the bimetallic catalyst component, the molar ratio of metal from the first catalyst component to the second catalyst component (e.g., molar ratio of Ti:Zr) is a value of from 0.1 to 20 in one embodiment; and from 1 to 18 in another embodiment, and from 2 to 15 in yet another embodiment, and from 3 to 12 in yet another embodiment; and from 4 to 10 in yet another embodiment, and from 4 to 8 in yet another embodiment; wherein a desirable molar ratio of first catalyst component metal:second catalyst component metal is any combination of any upper limit with any lower limit described herein.

Activators

As used herein, the term "activator" is defined to be any compound or combination of compounds, supported or unsupported, which can activate a single-site catalyst compound (e.g., metallocenes, Group 15 containing catalysts, etc.), such as by creating a cationic species from the catalyst component. Typically, this involves the abstraction of at least one leaving group (X group in the formulas/structures above) from the metal center of the catalyst component. The catalyst components of the present invention are thus activated towards olefin polymerization using such activators. Embodiments of such activators include Lewis acids such as cyclic or oligomeric poly(hydrocarbylaluminum oxides) and so called non-coordinating ionic activators ("NCA") (alternately, "ionizing activators" or "stoichiometric activators"), or any other compound that can convert a neutral metallocene catalyst component to a metallocene cation that is active with respect to olefin polymerization.

More particularly, it is within the scope of this invention to use Lewis acids such as alumoxane (e.g., "MAO"), modified alumoxane (e.g., "TIBAO"), and alkylaluminum compounds as activators, and/or ionizing activators (neutral or ionic) such as tri (n-butyl)ammonium tetrakis (pentafluorophenyl)boron and/or a trisperfluorophenyl boron metalloid precursors to activate desirable metallocenes described herein. MAO and other aluminum-based activators are well known in the art. Ionizing activators are well known in the art and are described by, for example, Eugene You-Xian Chen & Tobin J. Marks, *Cocatalysts for Metal-Catalyzed Olefin Polymerization: Activators, Activation Processes, and Structure-Activity Relationships* 100(4) CHEMICAL REVIEWS 1391–1434 (2000). The activators may be associated with or bound to a support, either in association with the catalyst component (e.g., metallocene) or separate from the catalyst component, such as described by Gregory G. Hlatky, *Heterogeneous Single-Site Catalysts for Olefin Polymerization* 100(4) CHEMICAL REVIEWS 1347–1374 (2000).

Non-limiting examples of aluminum alkyl compounds which may be utilized as activators for the catalyst precursor compounds for use in the methods of the present invention include trimethylaluminum, triethylaluminum, triisobutylaluminum, tri-n-hexylaluminum, tri-n-octylaluminum and the like.

Examples of neutral ionizing activators include Group 13 tri-substituted compounds, in particular, tri-substituted boron, tellurium, aluminum, gallium and indium compounds, and mixtures thereof. The three substituent groups are each independently selected from the group consisting of alkyls, alkenyls, halogen, substituted alkyls, aryls, arylhalides, alkoxy and halides. In one embodiment, the three groups are independently selected from the group consisting of halogen, mono or multicyclic (including halosubstituted) aryls, alkyls, and alkenyl compounds and mixtures thereof. In another embodiment, the three groups are selected from the group consisting of alkenyl groups having 1 to 20 carbon atoms, alkyl groups having 1 to 20 carbon atoms, alkoxy groups having 1 to 20 carbon atoms and aryl groups having 3 to 20 carbon atoms (including substituted aryls), and combinations thereof. In yet another embodiment, the three groups are selected from the group consisting of alkyls having 1 to 4 carbon groups, phenyl, naphthyl and mixtures thereof. In yet another embodiment, the three groups are selected from the group consisting of highly halogenated alkyls having 1 to 4 carbon groups, highly halogenated phenyls, and highly halogenated naphthyls and mixtures thereof By "highly halogenated", it is meant that at least 50% of the hydrogens are replaced by a halogen group selected from the group consisting of fluorine, chlorine and bromine. In yet another embodiment, the neutral stoichiometric activator is a tri-substituted Group 13 compound comprising highly fluorided aryl groups, the groups being highly fluorided phenyl and highly fluorided naphthyl groups.

In another embodiment, the neutral tri-substituted Group 13 compounds are boron compounds such as a trisperfluorophenyl boron, trisperfluoronaphthyl boron, tris(3,5-di(trifluoromethyl)phenyl)boron, tris(di-t-butylmethylsilyl)perfluorophenylboron, and other highly fluorinated trisarylboron compounds and combinations thereof, and their aluminum equivalents. Other suitable neutral ionizing activators are described in U.S. Pat. No. 6,399,532 B1, U.S. Pat. No. 6,268,445 B1, and in 19 ORGANOMETALLICS 3332–3337 (2000), and in 17 ORGANOMETALLICS 3996–4003 (1998).

Illustrative, not limiting examples of ionic ionizing activators include trialkyl-substituted ammonium salts such as triethylammonium tetra(phenyl)boron, tripropylammonium tetra(phenyl)boron, tri(n-butyl)ammonium tetra(phenyl) boron, trimethylammonium tetra(p-tolyl)boron, trimethylammonium tetra(o-tolyl)boron, tributylammonium tetra(pentafluorophenyl)boron, tripropylammonium tetra(o,p-dimethylphenyl)boron, tributylammonium tetra(m,m-dimethylphenyl)boron, tributylammonium tetra(p-trifluoromethylphenyl)boron, tributylammonium tetra(pentafluorophenyl)boron, tri(n-butyl)ammonium tetra(o-tolyl)boron and the like; N,N-dialkyl anilinium salts such as N,N-dimethylanilinium tetra(phenyl)boron, N,N-diethylanilinium tetra(phenyl)boron, N,N-2,4,6-pentamethylanilinium tetra(phenyl)boron and the like; dialkyl ammonium salts such as di-(isopropyl)ammonium tetra(pentafluorophenyl)boron, dicyclohexylammonium tetra(phenyl)boron and the like; and triaryl phosphonium salts such as triphenylphosphonium tetra(phenyl)boron, tri(methylphenyl)phosphonium tetra(phenyl)boron, tri(dimethylphenyl)phosphonium tetra(phenyl)boron and the like, and their aluminum equivalents.

In yet another embodiment of the activator of the invention, an alkylaluminum can be used in conjunction with a heterocyclic compound. The ring of the heterocyclic compound may includes at least one nitrogen, oxygen, and/or sulfur atom, and includes at least one nitrogen atom in one embodiment. The heterocyclic compound includes 4 or more ring members in one embodiment, and 5 or more ring members in another embodiment.

The heterocyclic compound for use as an activator with an alkylaluminum may be unsubstituted or substituted with one or a combination of substituent groups. Examples of suitable substituents include halogen, alkyl, alkenyl or alkynyl radicals, cycloalkyl radicals, aryl radicals, aryl substituted alkyl radicals, acyl radicals, aroyl radicals, alkoxy radicals, aryloxy radicals, alkylthio radicals, dialkylamino radicals, alkoxycarbonyl radicals, aryloxycarbonyl radicals, carbomoyl radicals, alkyl- or dialkyl-carbamoyl radicals, acyloxy radicals, acylamino radicals, aroylamino radicals, straight, branched or cyclic, alkylene radicals, or any combination thereof. The substituents groups may also be substituted with halogens, particularly fluorine or bromine, or heteroatoms or the like.

Non-limiting examples of hydrocarbon substituents include methyl, ethyl, propyl, butyl, pentyl, hexyl, cyclopentyl, cyclohexyl, benzyl or phenyl groups and the like, including all their isomers, for example tertiary butyl, isopropyl, and the like. Other examples of substituents include fluoromethyl, fluoroethyl, difluoroethyl, iodopropyl, bromohexyl or chlorobenzyl.

In one embodiment, the heterocyclic compound is unsubstituted. In another embodiment one or more positions on the heterocyclic compound are substituted with a halogen atom or a halogen atom containing group, for example a halogenated aryl group. In one embodiment the halogen is selected from the group consisting of chlorine, bromine and fluorine, and selected from the group consisting of fluorine and bromine in another embodiment, and the halogen is fluorine in yet another embodiment.

Non-limiting examples of heterocyclic compounds utilized in the activator of the invention include substituted and unsubstituted pyrroles, imidazoles, pyrazoles, pyrrolines, pyrrolidines, purines, carbazoles, and indoles, phenyl indoles, 2,5,-dimethylpyrroles, 3-pentafluorophenylpyrrole, 4,5,6,7-tetrafluoroindole or 3,4-difluoropyrroles.

In one embodiment, the heterocyclic compound described above is combined with an alkyl aluminum or an alumoxane to yield an activator compound which, upon reaction with a catalyst component, for example a metallocene, produces an active polymerization catalyst. Non-limiting examples of alkylaluminums include trimethylaluminum, triethylaluminum, triisobutylaluminum, tri-n-hexylaluminum, tri-n-octylaluminum, tri-iso-octylaluminum, triphenylaluminum, and combinations thereof.

Other activators include those described in WO 98/07515 such as tris (2, 2', 2"-nonafluorobiphenyl) fluoroaluminate. Combinations of activators are also contemplated by the invention, for example, alumoxanes and ionizing activators in combinations. Other activators include aluminum/boron complexes, perchlorates, periodates and iodates including their hydrates; lithium (2,2'-bisphenyl-ditrimethylsilicate)-

4THF; silylium salts in combination with a non-coordinating compatible anion. Also, methods of activation such as using radiation, electro-chemical oxidation, and the like are also contemplated as activating methods for the purposes of rendering the neutral metallocene-type catalyst compound or precursor to a metallocene-type cation capable of polymerizing olefins. Other activators or methods for activating a metallocene-type catalyst compound are described in for example, U.S. Pat. Nos. 5,849,852, 5,859,653 and 5,869,723 and WO 98/32775.

In general, the activator and catalyst component(s) are combined in mole ratios of activator to catalyst component from 1000:1 to 0.1:1 in one embodiment, and from 300:1 to 1:1 in a more particular embodiment, and from 150:1 to 1:1 in yet a more particular embodiment, and from 50:1 to 1:1 in yet a more particular embodiment, and from 10:1 to 0.5:1 in yet a more particular embodiment, and from 3:1 to 0.3:1 in yet a more particular embodiment, wherein a desirable range may include any combination of any upper mole ratio limit with any lower mole ratio limit described herein. When the activator is a cyclic or oligomeric poly(hydrocarbylaluminum oxide) (e.g., "MAO"), the mole ratio of activator to catalyst component ranges from 2:1 to 100,000:1 in one embodiment, and from 10:1 to 10,000:1 in another embodiment, and from 50:1 to 2,000:1 in a more particular embodiment. When the activator is a neutral or ionic ionizing activator such as a boron alkyl and the ionic salt of a boron alkyl, the mole ratio of activator to catalyst component ranges from 0.5:1 to 10:1 in one embodiment, and from 1:1 to 5:1 in yet a more particular embodiment.

More particularly, the molar ratio of Al/metallocene-metal (Al from MAO) ranges from 40 to 500 in one embodiment; and ranges from 50 to 400 in another embodiment; and ranges from 60 to 300 in yet another embodiment, and ranges from 70 to 200 in yet another embodiment; and ranges from 80 to 175 in yet another embodiment; and ranges from 90 to 125 in yet another embodiment, wherein a desirable molar ratio of Al(MAO) to metallocene-metal "M" can be any combination of any upper limit with any lower limit described herein.

Supports

A support may also be present as part of the bimetallic catalyst system of the invention. Supports, methods of supporting, modifying, and activating supports for single-site catalyst such as metallocenes is discussed in, for example, 1 METALLOCENE-BASED POLYOLEFINS 173–218 (J. Scheirs & W. Kaminsky eds., John Wiley & Sons, Ltd. 2000). The terms "support" or "carrier", as used herein, are used interchangeably and refer to any support material, a porous support material in one embodiment, including inorganic or organic support materials. Non-limiting examples of support materials include inorganic oxides and inorganic chlorides, and in particular such materials as talc, clay, silica, alumina, magnesia, zirconia, iron oxides, boria, calcium oxide, zinc oxide, barium oxide, thoria, aluminum phosphate gel, glass beads, and polymers such as polyvinylchloride and substituted polystyrene, functionalized or crosslinked organic supports such as polystyrene divinyl benzene polyolefins or polymeric compounds, and mixtures thereof, and graphite, in any of its various forms.

The support may be contacted with the other components of the catalyst system in any number of ways. In one embodiment, the support is contacted with the activator to form an association between the activator and support, or a "bound activator". In another embodiment, the catalyst component may be contacted with the support to form a "bound catalyst component". In yet another embodiment, the support may be contacted with the activator and catalyst component together, or with each partially in any order. The components may be contacted by any suitable means as in a solution, slurry, or solid form, or some combination thereof, and may be heated to any desirable temperature to effectuate a desirable chemical/physical transformation.

Desirable carriers are inorganic oxides that include Group 2, 3, 4, 5, 13 and 14 oxides and chlorides in one embodiment, and more particularly, inorganic oxides and chlorides of Group 13 and 14 atoms. Yet more particularly, support materials include silica, alumina, silica-alumina, magnesium chloride, graphite, and mixtures thereof. Other useful supports include magnesia, titania, zirconia, montmorillonite (EP 0 511 665 B1), phyllosilicate, and the like. Also, combinations of these support materials may be used, for example, silica-chromium, silica-alumina, silica-titania and the like. Additional support materials may include those porous acrylic polymers described in EP 0 767 184 B1.

In one aspect of the support useful in the invention, the support possess a surface area in the range of from 10 to 700 $m^2/g$, pore volume in the range of from 0.1 to 4.0 $cm^3/g$ and average particle size in the range of from 5 to 500 $\mu m$. In another embodiment, the surface area of the carrier is in the range of from 50 to 500 $m^2/g$, pore volume of from 0.5 to 3.5 $cm^3/g$ and average particle size of from 10 to 200 $\mu m$. In yet another embodiment, the surface area of the carrier is in the range is from 100 to 400 $m^2/g$, pore volume from 0.8 to 3.0 $cm^3/g$ and average particle size is from 5 to 100 $\mu m$. The average pore size of the carrier of the invention typically has pore size in the range of from 10 to 1000 Å, from 50 to 500 Å in another embodiment, and from 75 to 350 Å in yet another embodiment.

In one embodiment of the support, graphite is used as the support. The graphite is a powder in one embodiment. In another embodiment, the graphite is flake graphite. In another embodiment, the graphite and has a particle size of from 1 to 500 microns, from 1 to 400 microns in another embodiment, and from 1 to 200 in yet another embodiment, and from 1 to 100 microns in yet another embodiment.

Dehydration or calcining of the support may or may also be carried out. In one embodiment, the support is calcined prior to reaction with the fluorine or other support-modifying compound. In another embodiment, the support is calcined and used without further modification, or calcined, followed by contacting with one or more activators and/or catalyst components. Suitable calcining temperatures range from 100° C. to 1500° C. in one embodiment, and from 200° C. to 1200° C. in another embodiment, and from 300° C. to 1000° C. in another embodiment, and from 350° C. to 900° C. in yet another embodiment, and from 400° C. to 850° C. in yet a more particular embodiment, and from 800° C. to 900° C. in yet a more particular embodiment, and from 810° C. to 890° C. in yet a more particular embodiment, wherein a desirable range comprises any combination of any upper temperature limit with any lower temperature limit. Calcining may take place in the absence of oxygen and moisture by using, for example, an atmosphere of dry nitrogen.

The support, especially an inorganic support or graphite support, may be pretreated such as by a halogenation process or other suitable process that, for example, associates a chemical species with the support either through chemical bonding, ionic interactions, or other physical or chemical interaction. In one embodiment, the support is fluorided. The fluorine compounds suitable for providing fluorine for the support are desirably inorganic fluorine containing compounds. Such inorganic fluorine containing compounds may be any compound containing a fluorine atom as long as it does not contain a carbon atom. Particularly desirable are inorganic fluorine containing compounds selected from the group consisting of $NH_4BF_4$, $(NH_4)_2SiF_6$, $NH_4PF_6$, $NH_4F$, $(NH_4)_2TaF_7$, $NH_4NbF_4$, $(NH_4)_2GeF_6$, $(NH_4)_2SmF_6$, $(NH_4)_2TiF_6$, $(NH_4)_2ZrF_6$, $MoF_6$, $ReF_6$, $GaF_3$, $SO_2ClF$, $F_2$, $SiF_4$, $SF_6$, $ClF_3$, $ClF_5$, $BrF_5$, $IF_7$, $NF_3$, HF, $BF_3$, $NHF_2$ and $NH_4HF_2$.

A desirable method of treating the support with the fluorine compound is to dry mix the two components by blending at a concentration of from 0.01 to 10.0 millimole F/g of support in one embodiment, and in the range of from 0.05 to 6.0 millimole F/g of support in another embodiment, and in the range of from 0.1 to 3.0 millimole F/g of support in yet another embodiment. The fluorine compound can be dry mixed with the support either before or after charging to the vessel for dehydration or calcining the support. Accordingly, the fluorine concentration present on the support is in the range of from 0.2 to 5 wt % in one embodiment, and from 0.6 to 3.5 wt % of support in another embodiment.

Another method of treating the support with the fluorine compound is to dissolve the fluorine in a solvent, such as water, and then contact the support with the fluorine containing solution. When water is used and silica is the support, it is desirable to use a quantity of water that is less than the total pore volume of the support. Desirably, the support and, for example, fluorine compounds are contacted by any suitable means such as by dry mixing or slurry mixing at a temperature of from 100° C. to 1000° C. in one embodiment, and from 200° C. to 800° C. in another embodiment, and from 300° C. to 600° C. in yet another embodiment, the contacting in any case taking place for between two to eight hours.

It is within the scope of the present invention to co-contact (or "co-immobilize") more than one catalyst component with a support. Non-limiting examples of co-immobilization of catalyst components include two or more of the same or different metallocene catalyst components, one or more metallocene with a Ziegler-Natta type catalyst, one or more metallocene with a chromium or "Phillips" type catalyst, one or more metallocenes with a Group 15 containing catalyst, and any of these combinations with one or more activators. More particularly, co-supported combinations include metallocene A/metallocene A; metallocene A/metallocene B; metallocene/Ziegler Natta; metallocene/Group 15 containing catalyst; metallocene/chromium catalyst; metallocene/Ziegler Natta/Group 15-containing catalyst; metallocene/chromium catalyst/Group 15 containing catalyst, any of the these with an activator, and combinations thereof.

Further, the catalyst system of the present invention can include any combination of activators and catalyst components, either supported or not supported, in any number of ways. For example, the catalyst component may include any one or both of metallocenes and/or Group 15-containing catalysts components (e.g., U.S. Pat. No. 6,265,505; U.S. Pat. No. 5,707,913; EP 0 893 454; and WO 99/01460), and may include any combination of activators, any of which may be supported by any number of supports as described herein. Non-limiting examples of catalyst system combinations useful in the present invention include MN+NCA; MN:S+NCA; NCA:S+MN; MN:NCA:S; MN+AlA; MN:S+AlA; AlA:S+MN; MN:AlA:S; AlA:S+NCA+MN; NCA:S+MN+AlA; G15+NCA; G15:S+NCA; NCA:S+G15; G15:NCA:S; G15+AlA; G15:S+AlA; AlA:S+G15; G15:AlA:S; AlA:S+NCA+G15; NCA:S+G15+AlA; MN+NCA+G15; MN:S+NCA+G15; NCA:S+MN+G15; MN:NCA:S+G15; MN+G15+AlA; MN:S+AlA+G15; AlA:S+MN+G15; MN:AlA:S+G15; AlA:S+NCA+MN+G15; NCA:S+MN+AlA+G15; MN+NCA; G15:MN:S+NCA; G15:NCA:S+MN; G15:MN:NCA:S; G15:MN:S+AlA; G15:AlA:S+MN; G15:MN:AlA:S; G15:AlA:S+NCA+MN; G15:NCA:S+MN+AlA; MN+ZN+NCA; MN:S+ZN+NCA; NCA:S+ZN+MN; ZN:MN:NCA:S; MN+ZN+AlA; MN:ZN:S+AlA; AlA:S+ZN+MN; MN:AlA:ZN:S; AlA:ZN:S+NCA+MN; MN:AlA:S+ZN; wherein "MN" is metallocene component, "ZN" is a Ziegler-Natta catalyst component, such as described above for the first catalyst component, "NCA" is a non-coordinating activator including ionic and neutral boron and aluminum based compounds as described above, "AlA" is an aluminum alkyl and/or alumoxane based activator, "G15" is a Group 15-containing catalyst component as described above, and "S" is a support; and wherein the use of ":" with "S" means that that those groups next to the colon are associated with ("supported by") the support as by pretreatment and other techniques known in the art, and the "+" sign means that the additional component is not directly bound to the support but present with the support and species bound to the support, such as present in a slurry, solution, gas phase, or another way, but is not meant to be limited to species that have no physico-chemical interaction with the support and/or supported species. Thus, for example, the embodiment "MN:NCA:S+G15" means that a metallocene and NCA activator are bound to a support, and present in, for example, a gas phase polymerization with a Group 15 containing catalyst component.

In a particular embodiment, the catalyst system is selected from the group consisting of MN:ZN:NCA:S; MN:ZN:AlA:S; MN:AlA:S+ZN; ZN:AlA:S+MN; MN:NCA:S+ZN; and ZN:MN:AlA:NCA:S. The components may be combined in any order desirable to achieve the highest polymerization activity. In one embodiment, the ZN catalyst is immobilized prior to immobilizing the metallocene; in another embodiment, the metallocene is first immobilized, and in yet another embodiment, an activator is first immobilized, followed by either the metallocene and/or the ZN catalyst. In yet another embodiment, both the MN and ZN catalyst components are immobilized simultaneously on the support, the support being pretreated with activator in one embodiment, and treated after catalyst component treatment in yet another embodiment.

One embodiment of the support useful in the present invention is a so called "enhanced support", prepared by heating support particles at a dehydration temperature of at least 800° C. or more, and between 800° C. and 1000° C. in another embodiment, resulting in an enhanced support having a modified chemical structure. In a particular embodiment, the heating of the support takes place in an inert (e.g., $N_2$ or Ar) atmosphere, and in the absence of water. In preferred embodiments, increased productivity is achieved when the enhanced support is combined with the other parts of the bimetallic catalyst discussed herein, to form a supported bimetallic catalyst, which is then contacted with monomers during polymerization to produce a bimodal polyolefin compositions.

In one or more specific embodiments, an enhanced support is first prepared, preferably in the manner described below; then that enhanced support is treated (e.g., combined with ingredients that form the first catalyst) to provide a supported catalyst that includes the first catalyst component. In specific embodiments, that supported first catalyst is then treated in the presence of the second catalyst component to provide a supported bimetallic catalyst.

The enhanced support is prepared by any suitable means, and more particularly, by any means wherein water is removed from the support, such as by heating, exposure to low pressure, chemical treatment, or combinations thereof. Heating the support at a dehydration temperature of at least 800° C., and between 800° C. and 1000° C. in a particular embodiment, provides an enhanced support, for example, enhanced silica, which provides surprisingly improved results over support that is dehydrated at lower temperatures, that is, below 800° C., even slightly lower temperatures, for example, 760° C. While not immediately apparent from the enhancement procedure itself, it is contemplated that the heat treatment results in an actual chemical and/or physical change in the support structure itself, which only reveals its beneficial structure when combined with a first and second catalyst components described herein, and placed in the context of an actual polymerization. For example, when the enhanced silica is combined with both the first catalyst component and the second catalyst component to form a supported bimetallic catalyst composition, that supported bimetallic catalyst composition, including the enhanced silica, has been discovered as having desirably high productivity when used in a polymerization process for making bimodal polyolefin in a single reactor. For example, a productivity of at least 3000 grams polymer/gram catalyst can be achieved. More preferably, the bimetallic catalyst that includes the enhanced support has a productivity of at least 3500 grams polymer/gram catalyst. Even more preferably yet, a bimetallic catalyst having the enhanced support has a productivity of at least 4000 grams polymer/gram catalyst. Other specific embodiments of the invention include bimetallic catalysts with productivities of 4500 grams polymer/gram catalyst and above, 5000 grams polymer/gram catalyst and above, or even 6000 grams polymer/gram catalyst and above.

In a particular embodiment, the support useful in the present invention is a Group 13 or 14 inorganic oxide support having a pore volume ranging from 0.8 to 3 cm$^3$/g and a surface area of from 100 to 500 m$^2$/g. This support is desirably dehydrated as described herein in one embodiment. A preferred support is an amorphous high surface area silica, such as Davison 952 or Sylopol® 955, sold by Davison Chemical Division of W.R. Grace and Company. Those silicas are in spherical form, prepared by the spray drying process, with a surface area of 300 m$^2$/g and a pore volume of 1.65 cm$^3$/g. A procedure for dehydrating the silica at 600° C. is set forth in U.S. Pat. No. 5,525,678.

The enhanced support is then combined with a non-polar hydrocarbon diluent to form a support slurry, which can be stirred and optionally heated during mixing.

A variety of non-polar hydrocarbon diluents can be used to form the support slurry, but any non-polar hydrocarbon selected should remain in liquid form at all relevant reaction temperatures, and the ingredients used to form the first catalyst component should be at least partially soluble in the non-polar hydrocarbon. Accordingly, the non-polar hydrocarbon diluent is considered to be a "solvent" herein, even though in certain embodiments the ingredients are only partially soluble in the hydrocarbon.

Examples of suitable non-polar hydrocarbons include $C_4$–$C_{10}$ linear or branched alkanes, cycloalkanes and aromatics. More specifically, a non-polar alkane can be isopentane, hexane, isohexane, n-heptane, octane, nonane, or decane; a non-polar cycloalkane such as cyclohexane; or an aromatic such as benzene, toluene, or ethylbenzene. Mixtures of different non-polar hydrocarbons can also be used.

The support slurry can be heated both during and after mixing of the support particles with the non-polar hydrocarbon solvent, but at the point when either or both of the catalysts are combined with the support slurry, the temperature of the slurry should be sufficiently low so that neither of the catalysts are inadvertently deactivated. Thus, the temperature of the support slurry (e.g., silica slurry) is preferably maintained at a temperature below 90° C., for example, from 25 to 70° C., or from 40 to 60° C. in another embodiment.

Gas Phase Polymerization Process

The bimetallic catalysts, and more particularly, the supported bimetallic catalyst composition, described herein are preferably used to make bimodal polyolefin compositions, that is, compositions having a bimodal molecular weight distribution; in a particular embodiment, the bimetallic catalysts described herein are used in a single polymerization reactor to make the bimodal polyolefin composition. Once the supported bimetallic catalyst composition is prepared, as described above, a variety of processes can be carried out using that composition. Among the varying approaches that can be used include procedures set forth in U.S. Pat. No. 5,525,678 in which those processes are modified in accordance with the inventions claimed herein, for example, involving the high fluidized bulk density as described herein. The equipment, process conditions, reactants, additives and other materials will of course vary in a given process, depending on the desired composition and properties of the polymer being formed. For example, the processes discussed in any of the following patents can be used: U.S. Pat. Nos. 6,420,580; 6,388,115; 6,380,328; 6,359,072; 6,346,586; 6,340,730; 6,339,134; 6,300,436; 6,274,684; 6,271,323; 6,248,845; 6,245,868; 6,245,705; 6,242,545; 6,211,105; 6,207,606; 6,180,735; and 6,147,173.

More particularly, the process of the present invention is directed toward a gas phase polymerization process of one or more olefin monomers having from 2 to 30 carbon atoms, from 2 to 12 carbon atoms in a more particular embodiment, and from 2 to 8 carbon atoms in yet a more particular embodiment. The invention is particularly well suited to the polymerization of two or more olefin monomers of ethylene, propylene, 1-butene, 1-pentene, 1-hexene, 1-heptene, 1-octene, 1-nonene, 4-methyl-1-pentene, 1-isobutene, 1-isobutene and 1-decene.

Other monomers useful in the process of the invention include ethylenically unsaturated monomers, diolefins having 4 to 18 carbon atoms, conjugated or nonconjugated dienes, polyenes, vinyl monomers and cyclic olefins. Non-limiting monomers useful in the invention may include norbornene, norbornadiene, isobutylene, isoprene, vinylbenzocyclobutane, styrenes, alkyl substituted styrene, ethylidene norbornene, dicyclopentadiene and cyclopentene.

In the most preferred embodiment of the process of the invention, a copolymer of ethylene is produced, where with ethylene, a comonomer having at least one α-olefin having from 4 to 15 carbon atoms, from 4 to 12 carbon atoms in yet a more particular embodiment, and from 4 to 8 carbon atoms in yet a more particular embodiment, is polymerized in a gas phase process.

In another embodiment of the process of the invention, ethylene or propylene is polymerized with at least two different comonomers, optionally one of which may be a diene, to form a terpolymer.

Typically in a gas phase polymerization process a continuous cycle is employed where in one part of the cycle of a reactor system, a cycling gas stream, otherwise known as a recycle stream or fluidizing medium, is heated in the reactor by the heat of polymerization. This heat is removed from the recycle composition in another part of the cycle by a cooling system external to the reactor. Generally, in a gas fluidized bed process for producing polymers, a gaseous stream containing one or more monomers is continuously cycled through a fluidized bed in the presence of a catalyst under reactive conditions. The gaseous stream is withdrawn from the fluidized bed and recycled back into the reactor. Simultaneously, polymer product is withdrawn from the reactor and fresh monomer is added to replace the polymerized monomer. (See for example U.S. Pat. Nos. 4,543,399, 4,588,790, 5,028,670, 5,317,036, 5,352,749, 5,405,922, 5,436,304, 5,453,471, 5,462,999, 5,616,661 and 5,668,228.)

The reactor pressure in a gas phase process may vary from 100 psig (690 kPa) to 500 psig (3448 kPa) in one embodiment, from 200 psig (1379 kPa) to 400 psig (2759 kPa) in a more particular embodiment, and from 250 psig (1724 kPa) to 350 psig (2414 kPa) in yet a more particular embodiment.

The reactor temperature in a gas phase process may vary from 30° C. to 120° C. in one embodiment, from 60° C. to 115° C. in a more particular embodiment, from 70° C. to 110° C. in yet a more particular embodiment, and from 70° C. to 95° C. in yet a more particular embodiment, or as set out further below.

In an embodiment of the invention, the process is operated by introducing a carboxylate metal salt such as aluminum stearate or other metal-fatty acid compound into the reactor and/or contacting a carboxylate metal salt with the catalyst system of the invention prior to its introduction into the reactor.

The "catalyst system" useful in the gas phase polymerization process of the invention includes the first and second catalyst components, making up a bimetallic catalyst, and one or more activators. The bimetallic catalyst is activated by any suitable means known in the art, either before introduction into the polymerization reactor or in situ.

The gas-phase process of the present invention includes contacting the catalyst system (including catalyst components and activators, and optionally, a support) with monomers in a reactor vessel of desirable configuration to form a polyolefin. In one embodiment, the contacting may take place in a first reactor vessel, followed by transfer of the formed polymer into another second, third etc. reactor vessel to allow further polymerization, optionally by adding the same or different monomers and optionally by adding the same or different catalyst components, activators, etc. In a particular embodiment of the present invention, the bimetallic catalyst system is contacted with monomers in a single reactor vessel (or "reactor"), followed by isolation of a finished polyolefin resin.

For example, a gas phase polymerization process claimed herein may include use of a continuous cycle in which a cycling gas stream (i.e., a recycle stream or fluidizing medium) is heated in the reactor by the heat of polymerization. This heat can be removed from the recycle stream in another part of the cycle by a cooling system that is external to the reactor. In a gas fluidized bed process for producing polymers, a gaseous stream containing one or more monomers can be continuously cycled through a fluidized bed in the presence of a catalyst under reactive conditions. The gaseous stream is preferably withdrawn from the fluidized bed and then recycled back into the reactor. Polymer product can be withdrawn from the reactor and fresh monomer added to replace the polymerized monomer. (See for example U.S. Pat. Nos. 4,543,399, 4,588,790, 5,028,670, 5,317,036, 5,352,749, 5,405,922, 5,436,304, 5,453,471, 5,462,999, 5,616,661 and 5,668,228)

The reactor pressure in a gas phase process may vary from 100 psig (690 kPa) to 500 psig (3448 kPa) in one embodiment, from 200 psig (1379 kPa) to 400 psig (2759 kPa) in a particular embodiment, and from 250 psig (1724 kPa) to 350 psig (2414 kPa) in yet a more particular embodiment.

In one aspect of the invention, the voidage of the gas phase reactor is desirably controlled. In one embodiment, the polymerization process of the invention is characterized as a process of polymerization using a bimetallic catalyst wherein the voidage of the fluidized bed gas phase reactor is maintained at less than 40%. This can be accomplished by any suitable means such as by, for example, adjusting the hydrogen level in the reactor or reactors. The voidage of the reactor can be described in the equation below (A):

$$\text{Voidage} = \frac{SBD - FBD}{SBD - \text{gas density}} \quad (A)$$

wherein SBD is the "settled bulk density" of the formed resin granules in the reactor; FBD is the "fluidized bulk density", which is the density of the resin granules in the reactor; and "gas density" is simply the density of the gas in the reactor. The FBD is the ratio of the measured pressure drop upward across a centrally fixed portion of the reactor to the height of the fixed portion. As noted therein, the FBD is a mean value, which may be greater or less than the localized bulk density at any point in the fixed reactor portion. Since the gas density is diminishingly small, the equation describing voidage can be simplified to the following (B):

$$\text{Voidage} = 1 - \frac{FBD}{SBD} \quad (B)$$

Certain specific embodiments of the invention are advantageously directed to a process having fluidized bulk density (FBD) that is higher than other bimodal polyolefin polymerization processes. A high FBD (or low voidage) can have benefits in a gas phase polymerization process, since higher FBD generally means higher catalyst productivity due to the higher residence times allowable in such a reactor. A high FBD also provides for advantages for restarting a commercial-scale reactor when a gas phase polymerization cycle is interrupted by extraneous factors. For example, a low FBD corresponds to excessive bed expansion during the restarting process, and can sometimes even make the restart process unsuccessful.

As used herein, the term "fluidized bulk density" (FBD) has the same meaning given that same term in U.S. Pat. No. 5,436,304, in which the term is defined as the ratio of the measured pressure drop upward across a centrally fixed portion of the reactor to the height of the fixed portion, for example, a "pressure tap vertical separation." As noted therein, the FBD is a mean value, which may be greater or less than the localized bulk density at any point in the fixed reactor portion.

All FBD values that are absolute values of fluidized bulk density are expressed in units of $lbs/ft^3$. The values of FBD of the present invention range from 5 to 50 $lbs/ft^3$ in one embodiment, from 7 to 40 $lbs/ft^3$ in a more particular embodiment, and from 8 to 30 $lbs/ft^3$ in yet a more particular embodiment, and from 10 to 25 $lbs/ft^3$ in yet another embodiment, wherein a desirable range for FBD may be any combination of any upper limit with any lower limit.

All SBD values are expressed in units of lbs/ft³. The values of SBD of the present invention range from 10 to 60 lbs/ft³ in one embodiment, and from 12 to 50 lbs/ft³ in a more particular embodiment, and from 14 to 40 lbs/ft³ in yet another embodiment, and from 15 to 35 lbs/ft³ in yet another embodiment, wherein a desirable range for SBD may be any combination of any upper limit with any lower limit.

In one aspect of the invention, it is convenient to describe the value of FBD relative to that of SBD. In one embodiment of the invention, the FBD has a value of 60% or more of the SBD, and 65% or more in a more particular embodiment, and 70% or more in yet another embodiment, and 75% or more in yet a more particular embodiment. All FBD values that are expressed in terms of percentages (%) are fluidized bulk density as percentage of settled bulk density (SBD). Stated another way, FBD/SBD values of the present invention are 0.60 or more in one embodiment, 0.65 or more in another embodiment, and 0.70 or more in yet another embodiment, and 0.75 or more in yet a more particular embodiment.

It is desirable to adjust the polymerization process such that the voidage is at a desirable level. In one embodiment, the voidage is less than 40%, and less than 35% in a particular embodiment, and less than 30% in a more particular embodiment, and less than 20% in a more particular embodiment. It has been found that the voidage can be adjusted to a desirable level when using bimetallic catalyst systems comprising at least one metallocene by adjusting the level of hydrogen in the polymerization reactor. The level of hydrogen in the reactor can be adjusted by adjusting the level of hydrogen in the gas stream that is introduced into the reactor, or stated alternately, adjusting the ratio of hydrogen and ethylene.

In certain specific embodiments, the polymerization reactor temperature is maintained at a certain level to further optimize the voidage at a desirable level. As used herein, the term "reactor temperature" can refer to an actual measured temperature (i.e., at a point in time) of a fluidized bed in a reaction zone of a fluidized bed reactor used to carry out a gas phase polymerization; and can also refer to a calculated number that equals an average of a plurality of actual measured temperatures, measured intermittently over a period of time, for example, an average of ten measured temperatures over a four-hour period. In a particular embodiment, the polymerization reactor temperature ranges from 100° C., or 99° C., or 98° C., or 97° C., or 96° C., or 95° C., or 94° C., or 93° C., or 92° C., or 91° C., or 90° C., to 40° C., 50° C., 60° C., 70° C., or 80° C., or 82° C., or 84° C., or 86° C., or 88° C., or 90° C., wherein the reactor temperature may be in a range from any combination of any upper temperature limit with any lower temperature limit described herein. Thus, for example, a reactor temperature that averages 97° C. for at least a one, two, three, four or more-hour period may be utilized during a continuous gas phase polymerization cycle of the invention in one embodiment.

The voidage (or FBD) may be controlled in one embodiment by adjusting the hydrogen level in the polymerization process. The hydrogen levels (also referred to as hydrogen amounts) are sometimes expressed herein in terms of the molar ratio of $H_2$ to $C_2$ (also $H_2/C_2$ or $H_2:C_2$), wherein $H_2$ refers to molecular hydrogen, and $C_2$ refers to ethylene. Alternatively, the hydrogen levels discussed herein can refer to the ratio of moles $H_2$ to moles of monomers used in the polymerization reaction, for example, ethylene, propylene and/or butene. Preferably, however, the hydrogen level referenced herein is the molar ratio of hydrogen gas to ethylene monomers. As with reactor temperature, the hydrogen levels referenced herein and in the claims include actual instantaneous measured hydrogen levels, for example, a molar ratio of hydrogen gas to ethylene, or an average hydrogen level, based on measured hydrogen levels taken intermittently over a period of time.

The ratio of hydrogen to ethylene has an upper limit of 0.015 in one embodiment, and an upper limit of 0.01 in another embodiment, 0.009 in yet another embodiment, and 0.008 in a more particular embodiment, and 0.007 in yet a more particular embodiment, and 0.006 in yet a more particular embodiment, and 0.005 in yet a more particular embodiment, and 0.004 in yet a more particular embodiment. Thus, for example, the average ratio of a molecular hydrogen to ethylene over a four-hour period is 0.009 or below during a continuous gas phase polymerization cycle in one embodiment. The ratio of hydrogen to ethylene may have a lower limit of 0.0005 in another embodiment, and 0.001 in a more particular embodiment, and 0.002 in yet a more particular embodiment, and 0.003 in yet a more particular embodiment, and 0.004 in yet a more particular embodiment, and 0.005 in yet a more particular embodiment. The range of hydrogen levels (molar ratios of $H_2/C_2$) may have comprise any combination of any upper ratio limit with any lower ratio limit described herein. For example, in a specific embodiment, the molar ratio of the hydrogen gas in the gaseous stream to ethylene in the gaseous stream is from 0.003 to 0.009.

The invention can thus be described by any combination of the various embodiments described above. For example, the method of producing a fluorided metallocene catalyst component can be described by the reaction scheme (VI):

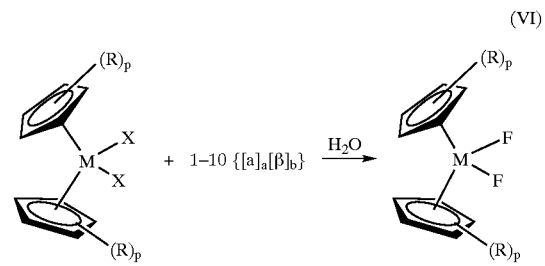

(VI)

wherein M is a Group 4, 5 or 6 metal in one embodiment; and zirconium or hafnium in a particular embodiment;

each X is independently selected from the group consisting of chloride, bromide, $C_1$ to $C_{20}$ carboxylates, $C_2$ to $C_{20}$ acetylacetonates, hydroxide and $C_1$ to $C_{10}$ alkoxides in one embodiment, and more particularly selected from the group consisting of the group consisting of chloride, bromide, $C_1$ to $C_{20}$ carboxylates, $C_2$ to $C_{20}$ acetylacetonates;

R are groups that may replace hydrides on the Cp rings and are independently selected from groups as defined above; and in a particular embodiment, selected from the group consisting of $C_1$ to $C_6$ alkyls;

p is an integer from 0 to 5 in one embodiment, and from 1 to 5 in a particular embodiment; wherein when p is 2 on any given Cp ring, adjacent R groups may form ring systems;

$[a]_a[\beta]_b$ is as defined above; and the reaction conditions are as defined above in one embodiment, and more particularly, comprise a two phase system, wherein one phase is an aqueous phase comprising at least 50 wt % water, at least 80% water in a particular embodiment; and the other phase comprising a hydrocarbon or halogenated hydrocarbon diluent.

The present invention also includes a bimetallic catalyst composition comprising at least one fluorided metallocene catalyst component as described herein, a non-metallocene catalyst component, and an activator, the catalyst components and activator supported on an inorganic oxide dehydrated at a temperature of greater than 800° C. The non-metallocene component, or "first catalyst component" is desirably a Ziegler-Natta catalyst component. The composition is formed in one embodiment by first synthesizing the fluorided metallocene as described above, followed by combining with the non-metallocene catalyst component, activator and support in any order. In one embodiment, the non-metallocene component is first combined with the support followed by an activator, followed then by combining with the fluorided metallocene catalyst produced by the method described herein.

The present invention also includes a process for producing a bimodal polyolefin composition comprising the steps of: (a) contacting a metallocene catalyst compound with an fluorinated inorganic salt for a time sufficient to form a fluorinated metallocene catalyst compound; next, (b) isolating the fluorided metallocene catalyst compound; followed by (c) combining the fluorided metallocene catalyst compound with an activator and ethylene monomers and optionally a support at from 50° C. to 120° C.; and (d)isolating polyethylene. The catalyst may be combined with other monomer such as 1-butene, 1-hexene, etc.

In one embodiment, the fluorided metallocene, activator and support are also combined with a Ziegler-Natta catalyst comprising titanium halide. This can be done in any desirable order to produce a bimetallic catalyst. In a particular embodiment, the fluorided metallocene, activator and support are combined and isolated prior to combining with ethylene monomers. The supported bimetallic catalyst is fed to the reactor in a dry (no diluent) state in a particular embodiment. In another embodiment, the bimetallic catalyst is suspended in a diluent (e.g., $C_5$ to $C_{15}$ hydrocarbon) comprising from 5 wt % to 100 wt % mineral oil or silicon oil and fed into the reactor. In a particular embodiment, the fluorinated inorganic salt is characterized in that it generates fluoride ions when contacted with a diluent that is at least 50 wt % water.

These embodiments of the present invention are exemplified by the following examples.

EXAMPLES

In the following examples, fourteen samples of fluorinated metallocene catalyst compounds were prepared. Each sample differed primarily in the chlorinated metallocene compound and the fluorinated inorganic salt used.

Example 1

Rac/meso-$(1,3\text{-MeBuCp})_2\text{ZrF}_2$ was prepared by adding a solution of 0.59 grams of (10.3 mmol, 4.47 eq.) $NH_4HF_2$ in 10 ml of water to a straw-colored solution of 1.00 gram of (2.31 mmol, 1.00 eq.) rac/meso-$(1,3\text{-MeBuCp})_2\text{ZrCl}_2$ in 10 ml of dichloromethane. The reaction mixture was stirred vigorously for 10 minutes, and the organic layer was separated. The organic layer was dried with $MgSO_4$, filtered, and evaporated in vacuo, leaving an off-white solid with a yield of 0.85 grams (92%). Rac/meso-$(1,3\text{-MeBuCp})_2\text{ZrF}_2$ was again prepared by adding a solution of 73.00 grams of (1.27 moles, 2.20 eq.) $NH_4HF_2$ in 500 ml of water to a brown solution of 250.00 grams of (0.578 moles, 1.00 eq.) rac/meso-$(1,3\text{-MeBuCp})_2\text{ZrCl}_2$ in 750 ml of toluene. The reaction mixture was stirred vigorously for 30 minutes, and the organic layer was separated. The organic layer was dried with $MgSO_4$, filtered, and evaporated in vacuo, leaving an off-white solid with a yield of 219.99 grams (95%).

Example 2

Rac-ethylene$(H_4\text{Ind})_2\text{ZrF}_2$ was prepared by adding a solution of 0.58 grams of (10.2 mmol, 4.34 eq.) $NH_4HF_2$ in 10 ml of water to a colorless solution of 1.00 gram of (2.31 mmol, 1.00 eq.) rac-Ethylene$(H_4\text{Ind})\text{ZrCl}_2$ in 50 ml of dichloromethane. The reaction mixture was stirred vigorously for 30 minutes, and the organic layer was separated. The organic layer was dried with $MgSO_4$, filtered, and evaporated in vacuo, leaving a white solid with a yield of 0.92 grams (100%).

Example 3

$(BuCp)_2\text{ZrF}_2$ was prepared by adding a solution of 14.46 grams of (254 mmol, 2.05 eq.) $NH_4HF_2$ in 60 ml of water to an amber solution of 50.00 grams of (124 mmol, 1.00 eq.) $(BuCp)_2\text{ZrCl}_2$ in 200 ml of dichloromethane. The reaction mixture was stirred vigorously for 22 minutes, and the organic layer was separated. The organic layer was dried with $MgSO_4$, filtered, and evaporated in vacuo, leaving a manila-colored solid with a yield 42.58 grams (93%).

Example 4

$(MeCp)_2\text{ZrF}_2$ was prepared by adding a solution of 0.39 grams of (6.84 mmol, 2.19 eq.) $NH_4HF_2$ in 10 ml of water to a colorless solution of 1.00 gram of (3.12 mmol, 1.00 eq.) $(MeCp)_2\text{ZrCl}_2$ in 10 ml of dichloromethane. The reaction mixture was stirred vigorously for 10 minutes, and the colorless organic layer was separated. The organic layer was dried with $MgSO_4$, filtered, and evaporated in vacuo, leaving a pale yellow-white solid with a yield 0.57 grams (64%).

Example 5

$(1,3\text{-Me}_2\text{Cp})_2\text{ZrF}_2$ was prepared by adding a solution of 0.36 grams of (6.31 mmol, 2.16 eq.) $NH_4HF_2$ in 10 ml of water to a light yellow solution of 1.02 grams of (2.93 mmol, 1.00 eq.) $(1,3\text{-Me}_2\text{Cp})_2\text{ZrCl}_2$ in 10 ml of dichloromethane. The reaction mixture was stirred vigorously for 11 minutes, and the colorless organic layer was separated. The organic layer was dried with $MgSO_4$, filtered, and evaporated in vacuo, leaving a pale yellow-white solid with a yield of 0.86 grams (95%).

Example 6

$Cp^*_2\text{ZrF}_2$ was prepared by adding a solution of 0.59 grams of (10.3 mmol, 4.39 eq.) $NH_4HF_2$ in 10 ml of water to a yellow solution of 1.02 grams of (2.36 mmol, 1.00 eq.) $Cp^*_2\text{ZrCl}_2$ in 10 ml of dichloromethane. The reaction mixture was stirred vigorously for 1 hour, and the yellow organic layer was separated. The organic layer was dried with $MgSO_4$, filtered, and evaporated in vacuo, leaving a light manila solid with a yield of 0.90 grams (96%).

Example 7

$(PrCp)_2\text{ZrF}_2$ was prepared by adding a solution of 0.63 grams of (11.0 mmol, 4.16 eq.) $NH_4HF_2$ in 10 ml of water to a straw-colored solution of 1.00 gram of (2.66 mmol, 1.00 eq.) $(PrCp)_2\text{ZrCl}_2$ in 10 ml of dichloromethane. The reaction mixture was stirred vigorously for 10 minutes, and the organic layer was separated. The organic layer was dried with $MgSO_4$, filtered, and evaporated in vacuo, leaving an off-white solid with a yield of 0.78 grams (86%). (PrCp)$_2$ZrF$_2$ was again prepared by adding a saturated solution of NaF in water (15 ml, approx. 15 mmol, 5–6 eq.) to a straw-colored solution of 1.00 gram of (2.66 mmol, 1.00 eq.) (PrCp)$_2$ZrCl$_2$ in 10 ml of dichloromethane. The reaction mixture was stirred vigorously for 10 minutes, and the organic layer was separated. The organic layer was dried with MgSO$_4$, filtered, and evaporated in vacuo, leaving an off-white solid with a yield of 0.90 grams (99%). (PrCp)$_2$ZrF$_2$ was yet again prepared by adding a solution of 1.97 grams of (11.1 mmol. 4.12 eq.) (NH$_4$)$_2$SiF$_6$ in 20 ml of water to a straw-colored solution of 1.00 gram of (2.66 mmol, 1.00 eq.) (PrCp)$_2$ZrCl$_2$ in 15 ml of dichloromethane. The reaction mixture was stirred vigorously for 18 minutes, and the organic layer was separated. The organic layer was dried with MgSO$_4$, filtered, and evaporated in vacuo, leaving an off-white solid with a yield of 0.80 grams (87%).

Example 8

(Me$_4$Cp)(PrCp)ZrF$_2$ was prepared by adding a solution of 0.60 grams of (10.5 mmol, 4.11 eq.) NH$_4$HF$_2$ in 10 ml of water to a straw-colored solution of 1.00 gram of (2.56 mmol, 1.00 eq.) (Me$_4$Cp)(PrCp)ZrCl$_2$ in 10 ml of dichloromethane. The reaction mixture was stirred vigorously for 10 minutes, and the organic layer was separated. The organic layer was dried with MgSO$_4$, filtered, and evaporated in vacuo, leaving an off-white solid with a yield of 0.90 grams (98%).

Example 9

Cp*(PrCp)ZrF$_2$ was prepared by adding a solution of 0.31 grams of (5.43 mmol, 2.20 eq.) NH$_4$HF$_2$ in 10 ml of water to a light yellow solution of 1.00 gram of (2.47 mmol, 1.00 eq.) Cp*(PrCp)ZrCl$_2$ in 10 ml of dichloromethane. The reaction mixture was stirred vigorously for 10 minutes, and the organic layer was separated. The organic layer was dried with MgSO$_4$, filtered, and evaporated in vacuo, leaving a white solid with a yield of 0.91 grams (99%). Cp* means pentamethylcyclopentadienyl.

Example 10

Cp(Me$_4$Cp)ZrF$_2$ was prepared by adding a solution of 0.36 grams of (5.96 mmol, 2.04 eq.) NH$_4$HF$_2$ in 8 ml of water to a light yellow solution of 1.00 gram of (2.93 mmol, 1.00 eq.) Cp(Me$_4$Cp)ZrCl$_2$ in 12 ml of dichloromethane. The reaction mixture was stirred vigorously for 10 minutes, and the organic layer was separated. The organic layer was dried with MgSO$_4$, filtered, and evaporated in vacuo, leaving a fluffy white solid with a yield of 0.91 grams (99%).

Example 11

Cp(PrMe$_4$Cp)ZrF$_2$ was prepared by adding a solution of 0.33 grams of (5.79 mmol, 2.19 eq.) NH$_4$HF$_2$ in 10 ml of water to a pale violet solution of 1.03 grams of (2.64 mmol, 1.00 eq.) Cp(PrMe$_4$Cp)ZrCl$_2$ in 10 ml of dichloromethane. The reaction mixture was stirred vigorously for 10 minutes, and the pale yellow organic layer was separated. The organic layer was dried with MgSO$_4$, filtered, and evaporated in vacuo, leaving a pale yellow-green liquid, with a yield of 0.80 grams (84%).

Example 12

Cp(1,3-MeBuCp)ZrF$_2$ was prepared by adding a solution of 0.32 grams of (5.61 mmol, 2.03 eq.) NH$_4$HF$_2$ in 10 ml of water to a dark brown solution of 1.00 gram of (2.76 mmol. 1.00 eq.) Cp(1,3-MeBuCp)ZrCl$_2$ in 10 ml of dichloromethane. The reaction mixture was stirred vigorously for 10 minutes, and the murky green organic layer was separated. The organic layer was dried with MgSO$_4$, filtered, and evaporated in vacuo, leaving a manila solid with a yield of 0.69 grams (76%).

Example 13

(PrCp)$_2$HfF$_2$ was prepared by adding a solution of 0.52 grams of (9.12 mmol, 4.19 eq.) NH$_4$HF$_2$ in 10 ml of water to a straw-colored solution of 1.01 grams of (2.18 mmol, 1.00 eq.) (PrCp)$_2$HfCl$_2$ in 10 ml of dichloromethane. The reaction mixture was stirred vigorously for 10 minutes, and the organic layer was separated. The organic layer was dried with MgSO$_4$, filtered, and evaporated in vacuo, leaving an amber solid with a greenish tinge, with a yield of 0.83 grams (89%).

Example 14

(Me$_4$Cp)$_2$HfF$_2$ was prepared by adding a solution of 1.20 grams (21.0 mmol, 10.3 eq.) NH$_4$HF$_2$ in 20 ml of water to a colorless solution of 1.00 gram of (2.03 mmol, 1.00 eq.) (Me$_4$Cp)$_2$HfCl$_2$ in 25 ml of dichloromethane. The reaction mixture was stirred vigorously for 1 hour, and the organic layer was separated. The colorless organic layer was dried with MgSO$_4$, filtered, and evaporated in vacuo, leaving a white solid with a yield of 0.91 grams (98%).

While the present invention has been described and illustrated by reference to particular embodiments, those of ordinary skill in the art will appreciate that the invention lends itself to many different variations not illustrated herein. For these reasons, then, reference should be made solely to the appended claims for purposes of determining the scope of the present invention. Further, certain features of the present invention are described in terms of a set of numerical upper limits and a set of numerical lower limits. It should be appreciated that ranges formed by any combination of these limits are within the scope of the invention unless otherwise indicated.

Unless otherwise indicated, all numbers expressing quantities of ingredients, properties, reaction conditions, and so forth, used in the specification and claims are to be understood as approximations based on the desired properties sought to be obtained by the present invention, and the error of measurement, etc., and should at least be construed in light of the number of reported significant digits and by applying ordinary rounding techniques. Notwithstanding that the numerical ranges and values setting forth the broad scope of the invention are approximations, the numerical values set forth are reported as precisely as possible.

All priority documents are herein fully incorporated by reference for all jurisdictions in which such incorporation is permitted. Further, all documents cited herein, including testing procedures, are herein fully incorporated by reference for all jurisdictions in which such incorporation is permitted.

What is claimed is:

1. A process of producing a fluorided catalyst compound, comprising contacting a metallocene catalyst compound with an fluorinated inorganic salt to form a fluorinated metallocene catalyst compound; wherein the fluorinated inorganic salt is in contact with a diluent comprising at least 10 wt % water.

2. The process of claim 1, wherein the fluorinated inorganic salt is characterized by generating fluoride ions when contacted with a diluent that is at least 50 wt % water.

3. The process of claim 1, wherein the fluorinated inorganic salt is described by the general formula:

$$[\alpha]_a[\beta]_b,$$

wherein α is a cationic species selected from the group consisting of Group 1 and 2 cations, anilinium and substituted versions thereof, and $NH_4^+$, $NH_3R$, $NH_2R_2$, and $NHR_3^+$ wherein R is selected from the group consisting of hydride, chloride, $C_1$ to $C_{10}$ alkyl and $C_6$ to $C_{12}$ aryls;

β is an anionic species selected from the group consisting of fluorine ions and moieties comprising fluorine and one or more elements selected from the group consisting of hydrogen, silicon, carbon, phosphorous, oxygen, aluminum and boron; and a and b are integers from 1 to 10.

4. The process of claim 1, wherein the inorganic salt is selected from the group consisting of $(NH_4)_3AlF_4$, $NH_4HF_2$, NaF, KF, $NH_4F$, $(NH_4)_2SiF_6$ and combinations thereof.

5. The process of claim 1, wherein the metallocene compound is described by the formulae:

$$Cp^A Cp^B MX_n, Cp^A MX_n \text{ and } Cp^A(A)Cp^B MX_n$$

wherein M is a Group 4, 5 or 6 atom;

$Cp^A$ and $Cp^B$ are each bound to M and are independently selected from the group consisting of cyclopentadienyl ligands, substituted cyclopentadienyl ligands, ligands isolobal to cyclopentadienyl and substituted ligands isolobal to cyclopentadienyl;

(A) is a divalent bridging group bound to both $Cp^A$ and $Cp^B$ selected from the group consisting of divalent $C_1$ to $C_{20}$ hydrocarbyls and $C_1$ to $C_{20}$ heteroatom containing hydrocarbonyls; wherein the heteroatom containing hydrocarbonyls comprise from one to three heteroatoms;

X is an anionic leaving group selected from the group consisting of chloride ions, bromide ions, carboxylates, acetylacetonates, and alkoxides; and n is an integer from 1 to 3.

6. The process of claim 1, wherein the metallocene compound is described by the formulae:

$$Cp^A Cp^B MX_a \text{ and } Cp^A(A)Cp^B MX_a$$

wherein M is zirconium or hafnium;

$Cp^A$ and $Cp^B$ are each bound to M and are independently selected from the group consisting of substituted cyclopentadienyl ligands, substituted indenyl ligands, substituted tetrahydroindenyl ligands, substituted fluorenyl ligands, and heteroatom derivatives of each; wherein the substituent groups are selected from the group consisting of $C_1$ to $C_{10}$ alkyls and halogens;

(A) is a divalent bridging group bound to both $Cp^A$ and $Cp^B$ selected from the group consisting of divalent $C_1$ to $C_{20}$ hydrocarbyls and $C_1$ to $C_{20}$ hetaroatom containing hydrocarbonyls; wherein the heteroatom containing hydrocarbonyls comprise from one to three heteroatoms;

X is an anionic leaving group selected from the group consisting of chloride ions, bromide ions, carboxylates, acetylacetonates, and alkoxides; and n is an integer from 1 to 3.

7. The process of claim 6, wherein at least one Cp is substituted.

8. The process of claim 6 wherein at least one Cp is disubstituted.

9. The process of claim 1, wherein the fluorinated metallocene has a productivity of at least 3,000 g polymer/g catalyst towards slurry or gas phase ethylene polymerization from 50° C. to 120° C.

10. The process of claim 1, wherein contacting the metallocene with the fluorinated inorganic salt comprises contacting the metallocene compound with from 2 to 20 equivalents of the fluorinated inorganic salt based on the number of equivalents of fluorine atom.

11. The process of claim 1, wherein the metallocene catalyst component is in contact with a hydrocarbon or halogenated hydrocarbon diluent.

12. A bimetallic catalyst composition comprising a fluorided metallocene catalyst component, a non-metallocene catalyst component, and an activator, the catalyst components and activator supported on an inorganic oxide dehydrated at a temperature of greater than 800° C.; characterized in that the fluorided metallocene catalyst compound is made by the method comprising contacting a metallocene catalyst compound with an fluorinated inorganic salt to form a fluorinated metallocene catalyst compound; wherein the fluorinated inorganic salt is in contact with a diluent comprising at least 10 wt % water.

13. The bimetallic catalyst composition of claim 12, wherein the fluorided metallocene compound is described by the formulae:

$$Cp^A Cp^B MX_n, Cp^A MX_n \text{ and } Cp^A(A)Cp^B MX_n$$

wherein M is a Group 4, 5 or 6 atom;

$Cp^A$ and $Cp^B$ are each bound to M and are independently selected from the group consisting of cyclopentadienyl ligands, substituted cyclopentadienyl ligands, ligands isolobal to cyclopentadienyl and substituted ligands isolobal to cyclopentadienyl;

(A) is a divalent bridging group bound to both $Cp^A$ and $Cp^B$ selected from the group consisting of divalent $C_1$ to $C_{20}$ hydrocarbyls and $C_1$ to $C_{20}$ heteroatom containing hydrocarbonyls; wherein the heteroatom containing hydrocarbonyls comprise from one to three heteroatoms;

at least one X is a fluoride ion; and n is an integer from 1 to 3.

14. The bimetallic catalyst composition of claim 12, wherein the metallocene compound is described by the formulae:

$$Cp^A Cp^B MX_n \text{ and } Cp^A(A)Cp^B MX_n$$

wherein M is zirconium or hafnium;

$Cp^A$ and $Cp^B$ are each bound to M and are independently selected from the group consisting of substituted cyclopentadienyl ligands, substituted indenyl ligands, substituted tetrahydroindenyl ligands, substituted fluorenyl ligands, and heteroatom derivatives of each; wherein the substituent groups are selected from the group consisting of $C_1$ to $C_{10}$ alkyls and halogens;

(A) is a divalent bridging group bound to both $Cp^A$ and $Cp^B$ selected from the group consisting of divalent $C_1$ to $C_{20}$ hydrocarbyls and $C_1$ to $C_{20}$ heteroatom containing hydrocarbonyls; wherein the heteroatom containing hydrocarbonyls comprise from one to three heteroatoms;

at least one X is a fluoride ion; and n is an integer from 1 to 3.

15. The bimetallic catalyst composition of claim 14, wherein at least one Cp is substituted.

16. The bimetallic catalyst composition of claim 14, wherein at least one Cp is disubstituted.

17. The bimetallic catalyst composition of claim 14, wherein at least one Cp has from 2 to 5 substitutions.

18. The bimetallic catalyst composition of claim 14, wherein the substituent groups are selected from the group consisting of methyl, ethyl, n-propyl, iso-propyl, n-butyl, iso-butyl, and tert-butyl.

19. The bimetallic catalyst composition of claim 12, wherein the non-metallocene catalyst is a Ziegler-Natta catalyst comprising a titanium halide.

20. The bimetallic catalyst composition of claim 12, wherein the inorganic oxide is dehydrated at a temperature of greater than 830° C.

21. The bimetallic catalyst composition of claim 12, wherein the inorganic oxide is silica.

22. A process for producing a bimodal polyolefin composition comprising the steps of:
   (a) contacting a metallocene catalyst compound with an fluorinated inorganic salt for a time sufficient to form a fluorinated metallocene catalyst compound; wherein the fluorinated inorganic salt is in contact with a diluent comprising at least 10 wt % water;
   (b) isolating the fluorided metallocene catalyst compound;
   (c) combining the fluorided metallocene catalyst compound with an activator and ethylene monomers and optionally a support at from 50° C. to 120° C.; and
   (d) isolating polyethylene.

23. The polymerization process of claim 22, wherein the fluorided metallocene, activator and support are also combined with a Ziegler-Natta catalyst comprising titanium halide.

24. The polymerization process of claim 22, wherein the fluorided metallocene, activator and support are combined and isolated prior to combining with ethylene monomers.

25. The polymerization process of claim 22, wherein the fluorinated inorganic salt is characterized by generating fluoride ions when contacted with a diluent that is at least 50 wt % water.

26. The polymerization process of claim 22, wherein the fluorinated inorganic salt is described by the general formula:

$$[\alpha]_a[\beta]_b,$$

wherein $\alpha$ is a cationic species selected from the group consisting of Group 1 and 2 cations; anilinium and substituted versions thereof; and $NH_4^+$, $NH_3R$, $NH_2R_2$, and $NHR_3^+$ wherein R is selected from the group consisting of hydride, chloride, $C_1$ to $C_{10}$ alkyl and $C_6$ to $C_{12}$ aryls;

$\beta$ an anionic species selected from the group consisting of fluorine ions and moieties comprising fluorine and one or more elements selected from the group consisting of hydrogen, silicon, carbon, phosphorous, oxygen, aluminum and boron; and a and b are integers from 1 to 10.

27. The polymerization process of claim 22, wherein the inorganic salt is selected from the group consisting of the group consisting of $(NH_4)_3AlF_6$, $NH_4HF_2$, NaF, KF, $NH_4F$, $(NH_4)_2SiF_6$ and combinations thereof.

28. The polymerization process of claim 22, wherein the metallocene compound is described by the formulae:

$$Cp^ACp^BMX_n, Cp^AMX_n \text{ and } Cp^A(A)Cp^BMX_n$$

wherein M is a Group 4, 5 or 6 atom;

$Cp^A$ and $Cp^B$ are each bound to M and are independently selected from the group consisting of cyclopentadienyl ligands, substituted cyclopentadienyl ligands, ligands isolobal to cyclopentadienyl and substituted ligands isolobal to cyclopentadienyl;

(A) is a divalent bridging group bound to both $Cp^A$ and $Cp^B$ selected from the group consisting of divalent $C_1$ to $C_{20}$ hydrocarbyls and $C_1$ to $C_{20}$ heteroatom containing hydrocarbonyls; wherein the heteroatom containing hydrocarbonyls comprise from one to three heteroatoms;

X is an anionic leaving group selected from the group consisting of chloride ions, bromide ions, carboxylates, acetylacetonates, and alkoxides; and n is an integer from 1 to 3.

29. The polymerization process of claim 22, wherein the metallocene compound is described by the formulas:

$$Cp^ACp^BMX_n \text{ and } Cp^A(A)Cp^BX_n$$

wherein M is zirconium or hafnium;

$Cp^A$ and $Cp^B$ are each bound to M and are independently selected from the group consisting of substituted cyclopentadienyl ligands, substituted indenyl ligands, substituted tetrahydroindenyl ligands, substituted fluorenyl ligands, and heteroatom derivatives of each; wherein the substituent groups are selected from the group consisting of $C_1$ to $C_{10}$ alkyls and halogens;

(A) is a divalent bridging group bound to both $Cp^A$ and $Cp^B$ selected from the group consisting of divalent $C_1$ to $C_{20}$ hydrocarbyls and $C_1$ to $C_{20}$ heteroatom containing hydrocarbonyls; wherein the heteroatom containing hydrocarbonyls comprise from one to three heteroatoms;

X is an anionic leaving group selected from the group consisting of chloride ions, bromide ions, carboxylates, acetylacetonates, and alkoxides; and n is an integer from 1 to 3.

30. The polymerization process of claim 22, wherein at least one Cp is substituted.

31. The polymerization process of claim 22, wherein at least one Cp is disubstituted.

* * * * *